United States Patent
Volgelstein et al.

(10) Patent No.: US 10,900,088 B2
(45) Date of Patent: *Jan. 26, 2021

(54) PERSONALIZED TUMOR BIOMARKERS

(71) Applicant: The Johns Hopkins University, Baltimore, MD (US)

(72) Inventors: Bert Volgelstein, Baltimore, MD (US); Kenneth W. Kinzler, Baltimore, MD (US); Victor Velculescu, Dayton, MD (US); Luis Diaz, Ellicot City, MD (US); Rebecca J. Leary, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/950,863

(22) Filed: Apr. 11, 2018

(65) Prior Publication Data

US 2018/0230550 A1 Aug. 16, 2018

Related U.S. Application Data

(63) Continuation of application No. 14/790,833, filed on Jul. 2, 2015, now Pat. No. 9,957,572, which is a continuation of application No. 13/579,964, filed as application No. PCT/US2011/025152 on Feb. 17, 2011, now abandoned.

(60) Provisional application No. 61/305,589, filed on Feb. 18, 2010.

(51) Int. Cl.
*C40B 30/00* (2006.01)
*C40B 20/04* (2006.01)
*C12Q 1/6886* (2018.01)

(52) U.S. Cl.
CPC ..... *C12Q 1/6886* (2013.01); *C12Q 2600/156* (2013.01)

(58) Field of Classification Search
CPC ...................................................... C12Q 1/68
See application file for complete search history.

(56) References Cited

U.S. PATENT DOCUMENTS

| | | | | |
|---|---|---|---|---|
| 6,785,614 B1* | 8/2004 | Collins | ............... | C12O 1/6827 435/6.16 |
| 2009/0061422 A1 | 3/2009 | Linke et al. | | |
| 2009/0275057 A1 | 11/2009 | Linke et al. | | |
| 2010/0112590 A1* | 5/2010 | Lo | ....................... | C12Q 1/6809 435/6.12 |
| 2013/0122010 A1* | 5/2013 | Campbell | ............ | C12Q 1/6809 424/141.1 |
| 2013/0210645 A1 | 8/2013 | Volgelstein et al. | | |

FOREIGN PATENT DOCUMENTS

| | | | | |
|---|---|---|---|---|
| WO | WO-03087830 A2 * | 10/2003 | ....... | G01N 33/57488 |
| WO | 2008/033782 | 3/2008 | | |
| WO | WO-2010014920 A1 * | 2/2010 | .......... | C12Q 1/6886 |
| WO | 2010/142467 | 12/2010 | | |
| WO | 2011/073665 | 6/2011 | | |

OTHER PUBLICATIONS

Campbell et al., Identification of Somatically Acquired Rearrangements in Cancer Using Genome-Wide Massively Parallel Paired-End Sequencing, Nature Genetics, 2008, 40(6), 722-729. (Year: 2008).*
Wang et al., Digital Karyotyping Identifies Thymidylate Synthase Amplification as a Mechanism of Resistance to 5-Fluorouracil in Metastatic Colorectal Cancer Patients, PNAS, 2004, 101(9),3089-3094. (Year: 2004).*
Campana D., Role of Minimal Residual Disease Monitoring in Adult and Pediatric Acute Lymphoblastic Leukemia, Author Manuscript, NIH Public Access, originally published Oct. 2009, 1-16. (Year: 2009).*
Fullwood et al., Next-Generation DNA Sequencing of Paired-End Tags (PET) for Transcriptome and Genome Analyeses, Genome Research, 2009, 19, 521-532. (Year: 2009).*
Balachandar et al., "Identification of a high frequency of chromosomal rearrangements in the centromeric regions of prostate cancer patients," Journal of Zhejiang University-Science B, vol. 8, No. 9, Sep. 2007, pp. 538-646.
Bashir et al., "Evaluation of Paired-End Sequencing Strategies for Detection of Genome Rearrangements in Cancer," PLoS Computational Biology, 2008, 4(4), 1-14.
Bignell et al., "Architectures of somatic genomic rearrangement in human caner amplicons at sequence-level resolution," *Genome Research* 17:1296-1303 (2007).
Bregni et al., "Minimal residual disease in acute lymphoblastic leukemia detected by immune selection and gene rearrangement analysis," *J Clin Oncol* 7, 338-343 (1989).
C. A. Maher, C. Kumar-Sinha, X. Cao, S. Kalyana-Sundaram, B. Han, X. Jing, L. Sam, T. Barrette, N. Palanisamy, A. M. Chinnaiyan, Transcriptome sequencing to detect gene fusions in cancer. Nature 458, 97-101 (2009).
C. Lengauer, K. W. Kinzler, B. Vogelstein, Genetic instabilities in human cancers. Nature 396, 643-649 (1998).

(Continued)

*Primary Examiner* — Amy M Bunker
(74) *Attorney, Agent, or Firm* — Fish & Richardson P.C.

(57) ABSTRACT

Clinical management of human cancer is dependent on the accurate monitoring of residual and recurrent tumors. We have developed a method, called personalized analysis of rearranged ends (PARE), which can identify translocations in solid tumors. Analysis of four colorectal and two breast cancers revealed an average of nine rearranged sequences (range 4 to 15) per tumor. Polymerase chain reaction with primers spanning the breakpoints were able to detect mutant DNA molecules present at levels lower than 0.001% and readily identified mutated circulating DNA in patient plasma samples. This approach provides an exquisitely sensitive and broadly applicable approach for the development of personalized biomarkers to enhance the clinical management of cancer patients.

15 Claims, 6 Drawing Sheets

Specification includes a Sequence Listing.

(56) References Cited

OTHER PUBLICATIONS

Campbell et al., Identification of Somatically Aquired Rearrangements in Cancer Using Genome-Wide Massively Parallel Paired-End Sequencing, Nature Genetics, 2008, 40(6), 722-729.
Chiang et al., "High-resolution mapping of copy-number alterations with massively parallel sequencing," *Nat Methods* 6, 99-103 (2009).
Clark Michael James et al., "U87MG Decoded: The Genomic Sequence of a Cy logenetically Aberrant Human Cancer Cell Line," PLOS Genetics, vol. 6, No. 1, Jan. 2010, pp. 1-16, XP002698940, ISSN: 1553-7390.
Cuffy et al., Management of Less Common Tumors of the Colon, Rectum and Anus, Clinical Colorectal Cancer, 2006, 5(5), 327-337.
David J. McBride et al., "Use of cancer-specific genomic rearrangements to quantify disease burden in plasma from patients with solid tumors," Genes, Chromosomes and Cancer, vol. 49, No. 11, Nov. 19, 2010, pp. 1062-1069, XP55064914, ISSN: 1045-2257.
Di et al., "Identification of OTX2 as a medulloblastoma oncogene whose product can be targeted by all-trans retinoic acid," Cancer Res 65, 919-924 (2005).
Diehl et al., "Detection and quantification of mutations in the plasma of patients with colorectal tumors," Proceedings of The National Academy of Sciences, USA, vol. 102, No. 45, Nov. 8, 2005, pp. 16368-16373, XP007809665.
Diehl, D. Dressman, B. Vogelstein, K. W. Kinzler, BEAMing up for detection and quantification of rare sequence variants. *Nat Methods* 3, 95-97 (2006).
Dressman et al., "Transforming single DNA molecules into fluorescent magnetic particles for detection and enumeration of genetic variations," *Proc Natl Acad Sci USA* 100, 8817-8822 (2003).
Erin D. Pleasance et al., "A comprehensive catalogue of somatic mutations from a human cancer genome," Nature, vol. 463, No. 7278, Jan. 14, 2010, pp. 191-196, XP55065443, ISSN: 0028-0836.
Erin D. Pleasance et al., "A small-cell lung cancer genome with complex signatures of tobacco exposure," Nature, vol. 463, No. 7278, Jan. 14, 2010, pp. 184-190, XP55065776, ISSN: 0028-0836.
Extended European Search Report dated Jul. 4, 2013, issued in related European Application No. 11745196.3.
F. Mitelman, B. Johansson, F. Mertens, The impact of translocations and gene fusions on cancer causation. Nat Rev Cancer 7, 233-245 (2007).
Frank Diehl et al., "Circulating mutant DNA to assess tumor dynamics," Nature Medicine, Nature Publishing Group, New York, NY, US, vol. 14, No. 9, Sep. 1, 2008, pp. 985-990, XP002666722, ISSN: 1078-8956.
Grimwade et al., "Prospective minimal residual disease monitoring to predict relapse of acute promyelocytic leukemia and to direct pre-emptive arsenic trioxide therapy," *J Clin Oncol* 27, 3650-3658 (2009).
Hughes et al., "Monitoring CML patients responding to treatment with tyrosine kinase inhibitors: review and recommendations for harmonizing current methodology for detecting BCR-ABL transcripts and kinase domain mutations and for expressing results," Blood 108, 28-37 (2006).
International Search Report and Written Opinion dated Dec. 14, 2011 in related International Application No. PCT/US2011/025152.
International Search Report received in corresponding European Application No. 11745196.3 dated Jul. 4, 2013.
Kevin Judd Mckernan et al., "Sequence and structural variation in a human genome uncovered by short-read, massively parallel ligation sequencing using two-based encoding," Genome Research, Cold Spring Harbor Laboratory Press, Woodbury, NY, US, vol. 19, No. 9, Sep. 1, 2009, pp. 1527-1541, XP002626908, ISSN: 1088-9051.
Korbel et al., "Paired-end mapping reveals extensive structural variation in the human genome," *Science* 318, 420-426 (2007).
Kulasingam et al., Tissue Culture-Based Breast Cancer Biomarker Discovery Platform, Int. J. Cancer, 2008, 123, 2007-2012.

Leary et al., Development of Personalized Tumor Biomarkers Using Massively Parallel Sequencing, Cancer Genetics, 2010, 2(20), 1-9.
Lucito et al., "Representational oligonucleotide microarray analysis: a high-resolution method to detect genome copy number variation," Genome Res 13, 2291-2305 (2003).
Mattarucchu E et al., "Molecular monitoring of residual disease in chronic myeloid leukemia by genomic DNA compared with conventional mRNA analysis," Journal of Molecular Diagnostics, The American Society for Investigative Pathology, US, vol. 11, No. 5, Sep. 1, 2009, pp. 482-487, XP008125605, ISSN: 1525-1578.
Michael J. Duffy et al., "A Personalized Approach to Cancer Treatment: How Biomarkers Can Help," Clinical Chemistry, 2008, vol. 54, No. 11, pp. 1770-1779.
Mitch Dowsett et al., "Emerging Biomarkers and New Understanding of Traditional Markers in Personalized Therapy for Breast Cancer," Clin Cancer Res., 2008, vol. 14, No. 24, pp. 8019-8026.
Nakayama et al., "Homozygous deletion of MKK4 in ovarian serous carcinoma," Cancer Biol Ther 5, 630-634 (2006).
Non-Final Office Action issued in corresponding U.S. Appl. No. 13/579,964 dated Feb. 15, 2017.
Office Action dated Jan. 22, 2016 issued in related European Application No. 11745196.3.
Office Action dated Jan. 11, 2016 in related U.S. Appl. No. 14/790,833.
Office Action dated Jun. 14, 2016 in related U.S. Appl. No. 141790,833.
Peiffer et al., "High-resolution genomic profiling of chromosomal aberrations using Infinium whole-genome genotyping," *Genome Res* 16, 1136-1148 (2006).
Peter J. Campbell et al., "Identification of somatically acquired rearrangements in cancer using genome-wide massively parallel paired-end sequencing," Nature Genetics, Nature Publishing Group, US, vol. 40, No. 6, Jun. 1, 2008, pp. 722-729, XP002622046, ISSN: 1546-1718.
Philip J. Stephens et al., "Complex landscapes of somatic rearrangement in human breast cancer genomes," Nature, vol. 462, No. 7276, Dec. 24, 2009, pp. 1005-1010, XP55064910, ISSN: 0028-0836.
Pinkel et al., High resolution analysis of DNA copy number variation using comparative genomic hybridization to microarrays. Nat Genet 20, 207-211. (1998).
Primer 3 v. 0.4.0. "Pick Primers from a DNA Sequence" http://frodo.wi.mit.edu/primer3/.
R. J. Leary et al., "Integrated analysis of homozygous deletions, focal amplifications, and sequence alterations in breast and colorectal cancers," Proceedings of The National Academy of Sciences, vol. 105, No. 42, Oct. 1, 2008, pp. 16224-16229, XP055044922, ISSN: 0027-8424.
R.J. Leary et al., "Development of Personalized Tumor Biomarkers Using Massively Parallel Sequencing," Science Translation Medicine, vol. 2, No. 20, Feb. 24, 2010, pp. 20ra14-20ra14, XP55064908, ISSN: 1946-6234.
Shendure et al., "Accurate multiplex polony sequencing of an evolved bacterial genome," *Science* 309, 1728-1732 (2005).
Sjoblom et al., "The consensus coding sequences of human breast and colorectal cancers," *Science* 314, 268-274 (2006).
SOLiD Data format and File Definitions Guide. http://www3.appliedbiosystems.com/ ems/ groups/mcb marketing/documents/generaldocuments/ ems_ 05 8717. pdf.
Sun et al., Chromosomal Rearrangements Between Serotype A and D Strains in Cryptococcus Neoformans, PLoS One, 2009, 4(5), 1-17.
T. Lion, Minimal residual disease. Curr Opin Hematol 6, 406-411 (1999).
Van der Velden et al., "Optimization of PCR-based minimal residual disease diagnostics for childhood acute lymphoblastic leukemia in a multi-center setting," *Leukemia* 21, 706-713 (2007).
Wang et al., "Digital karyotyping identifies thymidylate synthase amplification as a mechanism of resistance to 5-fluorouracil in metastatic colorectal cancer patients," *Proc Natl Acad Sci USA* 101, 3089-3094 (2004).

* cited by examiner

| ALTERATION | SAMPLE | FORWARD TAG | | REVERSE TAG | | REARRANGEMENT TYPE |
|---|---|---|---|---|---|---|
| | | CHROMOSOME | POSITION | CHROMOSOME | POSITION | |
| A | B5 | 11 | 57,714,122 | 8 | -48,889,091 | INTERCHROMOSOMAL |
| B | B5 | 20 | 29,591,563 | 18 | -19,142,112 | INTERCHROMOSOMAL |
| C | B7 | 5 | 38,284,430 | 10 | -44,715,202 | INTERCHROMOSOMAL |
| D | B7 | 6 | -90,854,024 | 6 | -106,401,711 | INTRACHROMOSOMAL |
| E | Co108 | 3 | 60,573,270 | 3 | 60,473,213 | INTRACHROMOSOMAL |
| F | Co108 | 4 | 81,934,151 | 15 | 54,039,041 | INTERCHROMOSOMAL |
| G | Co84 | 8 | 128,442,121 | 19 | 49,144,200 | INTERCHROMOSOMAL |
| H | Co84 | 13 | -109,267,878 | 11 | -34,791,081 | INTERCHROMOSOMAL |

US 10,900,088 B2

PERSONALIZED TUMOR BIOMARKERS

CROSS-REFERENCE TO RELATED APPLICATIONS

The present application is a continuation of U.S. non-provisional application Ser. No. 14/790,833, filed Jul. 2, 2015, issued on May 1, 2018, as U.S. Pat. No. 9,957,572, which is a division of U.S. non-provisional application Ser. No. 13/579,964, filed Jan. 7, 2013, now abandoned, which is a 35 U.S.C. § 371 national phase application of PCT application number PCT/US2011/25152, filed Feb. 17, 2011, which claims the benefit of and priority to U.S. provisional patent application Ser. No. 61/305,589, filed Feb. 18, 2010, the content of each of which is incorporated by reference herein in its entirety.

This invention was made with government support under grants CA121113, CA057345, CA62924, and CA043460 awarded by the National Institutes of Health. The government has certain rights in the invention.

TECHNICAL FIELD OF THE INVENTION

This invention is related to the area of cancer detection and management. In particular, it relates to identification and use of somatic rearrangements as markers of a person's cancer.

BACKGROUND OF THE INVENTION

A nearly universal feature of human cancer is the widespread rearrangement of chromosomes as a result of chromosomal instability (1). Such structural alterations begin to occur at the earliest stages of tumorigenesis and persist throughout tumor development. The consequences of chromosomal instability can include copy number alterations (duplications, amplifications and deletions), inversions, insertions, and translocations (2). Historically, the ability to detect such alterations has been limited by the resolution of genetic analyses. However, a number of more recent approaches including high density oligonucleotide arrays and high throughput sequencing have allowed detection of changes at much higher resolution (3-15).

Tumor-specific (somatic) chromosomal rearrangements have the potential to serve as highly sensitive biomarkers for tumor detection. Such alterations are not present in normal cells and should be exquisitely specific. Rearrangement-associated biomarkers therefore offer a reliable measure that would be useful for monitoring tumor response to specific therapies, detecting residual disease after surgery, and for long-term clinical management. Recurrent somatic structural alterations, such as those involving the BCR-ABL oncogene (the target of the Philadelphia chromosome translocation), immunoglobulin (Ig) genes, T cell receptor (TCR) genes, and the retinoic acid receptor alpha (RARα) gene, have been shown to be useful as diagnostic markers in certain hematopoietic malignancies (16-20). However, recurrent structural alterations do not generally occur in most solid tumors. There is a continuing need in the art to develop tools for diagnosing and monitoring cancers.

SUMMARY OF THE INVENTION

According to one aspect of the invention a method is provided for identifying a personalized tumor marker for a cancer patient. A mate-paired library is made from tumor DNA of the patient. Mate pairs of the library comprise two genomic tags that are co-linear but not contiguous in a segment of the tumor DNA. Sequence of a plurality of mate pairs of the library is determined. Regions of copy number differences among regions in the tumor DNA of the patient are determined. Mate paired tags which map within a region of copy number difference or spanning a boundary of copy number difference are identified as potential markers of a tumor-specific DNA rearrangement in the cancer patient.

According to another aspect of the invention a method is provided for assessing or detecting tumor in a patient. A DNA fragment is amplified using a template from the patient's tissues or body fluids and primers that span a patient-specific, tumor-specific rearrangement breakpoint. The rearrangement breakpoint is between genes involved in rearrangements in <1% of tumors of patients with the same type of tumor. The amount or proportion of amplified DNA fragment in the patient's tissue or body fluid is determined.

Another aspect of the invention is another method of identifying a personalized tumor marker for a cancer patient. Sequence of two ends of each of a plurality of fragments of DNA from the cancer patient is determined. Regions of copy number differences among regions in the tumor DNA of the patient are determined. Fragments of the plurality of fragments which map within a region of copy number difference or spanning a boundary of copy number difference are identified as potential markers of a tumor-specific DNA rearrangement in the cancer patient.

A further aspect of the invention is another method of identifying a personalized tumor marker for a cancer patient. A plurality of mate paired tags of a library of mate paired tags is tested by comparing to non-tumor DNA or to sequence of non-tumor DNA. Each of the mate paired tags comprises two genomic tags that are co-linear but not contiguous in a segment of tumor DNA of the cancer patient. A tumor-specific DNA rearrangement is identified if the two genomic tags of a mate paired tag are at different locations or in a different orientation within a chromosome or on different chromosomes of non-tumor DNA compared to tumor DNA.

Yet another aspect of the invention is another method of identifying a personalized tumor marker for a cancer patient. Two ends of a plurality of fragments of tumor DNA of the cancer patient are tested by comparing to non-tumor DNA or to sequence of non-tumor DNA. A tumor-specific DNA rearrangement is identified if the ends of a fragment are at different locations or in a different orientation within a chromosome or on different chromosomes of non-tumor DNA compared to tumor DNA.

Still another aspect of the invention is a method of screening for a cancer in a human. A plurality of mate paired tags of a library of mate paired tags is tested by comparing to normal DNA or to sequence of normal DNA. Each of the mate paired tags comprises two genomic tags that are co-linear but not contiguous in a segment of DNA in the blood of the human. A DNA rearrangement is identified if the two genomic tags of a mate paired tag are at different locations or in a different orientation within a chromosome or on different chromosomes of normal DNA compared to blood DNA. The presence of a DNA rearrangement suggests the presence of a cancer in the human.

A further aspect of the invention is a method of screening for a cancer in a human. Two ends of a fragment of blood DNA of the human are tested by comparing to normal DNA or to sequence of normal DNA. A DNA rearrangement is identified if the ends are at different locations or in a different orientation within a chromosome or on different chromosomes of normal DNA compared to blood DNA. The presence of a DNA rearrangement suggests the presence of a cancer in the human.

An additional aspect of the invention is a kit for monitoring presence or amount of a breakpoint in a somatic DNA rearrangement in tumor DNA of a patient. The kit may comprise one or more pairs of amplification primers. Each pair is complementary to priming sites on opposite sides of a breakpoint. The priming sites are separated by less than 200 basepairs in the tumor DNA. The DNA rearrangement occurs in <1% of tumors of patients with the same type of tumor.

These and other embodiments which will be apparent to those of skill in the art upon reading the specification provide the art with methods for detecting and monitoring cancers in the body.

BRIEF DESCRIPTION OF THE DRAWINGS

FIG. 4A. The identified chromosome 4/8 and 16 rearrangements were used to design PCR primers spanning breakpoints and used to amplify rearranged DNA from tumor tissue and plasma from patients Hx402 and Hx403, respectively. A plasma sample from an unrelated healthy individual was used as a control for both rearrangements. FIG. 4B. Plasma samples from patient Hx402 were analyzed at different time points using digital PCR to determine the fraction of genomic equivalents of plasma DNA containing the chromosome 4/8 rearrangement. The fraction of rearranged DNA at day 137 was 0.3%, consistent with residual metastatic lesions present in the remaining lobe of the liver.

DETAILED DESCRIPTION OF THE INVENTION

Figure 1:
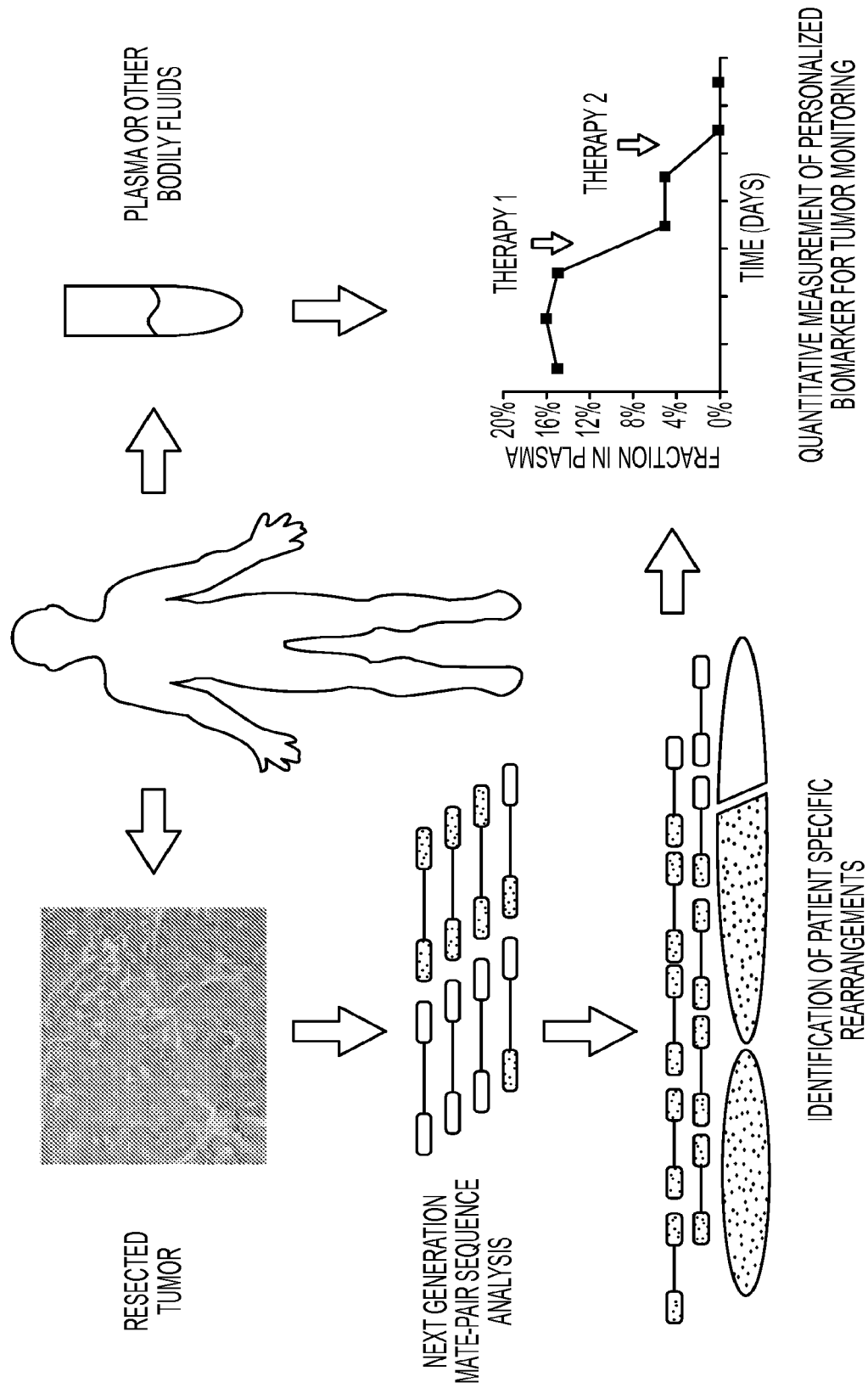
FIG. 1. Schematic of "Personalized Analysis of Rearranged Ends (PARE)" approach. The method is based on next generation mate-paired analysis of, e.g., resected tumor DNA to identify individualized tumor-specific rearrangements. Such alterations are used to develop PCR based quantitative analyses for personalized tumor monitoring of plasma samples or other bodily fluids.

We have found that any structural alteration identified in an individual's tumor can be used as a tumor marker, even if it is not found in tumors of the same type in other individuals and even if it is not a "driver"—causing a selective growth advantage—but merely a "passenger." Moreover, such markers can be used to detect tumor and or quantify the tumor burden in an individual by assessment of blood.

Somatic rearrangements are a focus of the present invention. Such rearrangements are used as markers of a tumor. In particular, the boundaries of the rearrangments can be detected and used as a quantitative or qualitative indicator of the tumor. Because the boundaries are unique to the tumor DNA, they should be exquisitely specific markers of the tumor. Somatic rearrangements can be detected using any method known in the art. One particularly useful method is a technique called digital karyotyping. This technique identifies changes in copy number across regions or windows in the genome. Other methods may employ commercially available arrays to detect regions of copy number differences among regions of a genome. The copy number differences reflect a rearrangement, such as a deletion or amplification, and an amplification can further harbor other rearrangements within it. Once a somatic rearrangement is identified, one or more of its boundaries (also referred to as breakpoints) can be identified and that boundary can be a very specific marker for the tumor. Identifying a boundary can be accomplished by a number of techniques.

In one technique mate-paired genomic tags are tested to determine different copy numbers of one member of the pair compared to the other. A different copy number between two members suggests that the tags span a rearrangement breakpoint or boundary. The mate-pairs are typically derived from a single fragment that is processed to yield two smaller portions that can be more readily sequenced or analyzed. An intervening segment is typically removed, leaving the two smaller portions linked on a single molecule in the same orientation that they were found in the tumor genome.

A similar technique does not involve mate-pairs but involves sequencing and/or analyzing two different portions or ends of a single fragment of genomic DNA from a tumor. The two portions or ends may be separated by any distance, from immediately adjacent up to 1 kb, 1.5 kb, 2 kb, or 3 kb, for example. The ends may not be the literal ends of a fragment, but may be close to the ends or merely two non-overlapping portions. The sequence of the two ends may be determined separately, for example from either end, or the sequence can be determined in one direction and analyzed for separate, non-overlapping segments of differing copy numbers.

Amplification primers are known in the art and typically comprise between 15 and 50 nucleotides which are complementary to a template. A pair of primers is complementary to opposite strands of a template and can amplify a double stranded fragment that contains the two primer sequences in addition to sequences which are between them on the template. From 0 to 10, 20, 50, 100, 200, 500, 1000, 1500, or 2000 basepairs or nucleotides may lie between the two primer-complementary sequences on the template. According to the invention, each primer will hybridize to opposite sides of a rearrangement boundary. These primers are also referred to as spanning or flanking the breakpoint, because the amplicon that they generate will span and/or flank the breakpoint. Optionally, a primer may contain the boundary junction. Primers need not be 100% complementary to template, but may incorporate other bases or sequences of bases for other purposes, such as to facilitate purification or downstream processing.

Once tumor-specific breakpoints are ascertained for an individual patient, primers can be prepared and shipped elsewhere for use. For example pairs or panels of pairs of primers can be packaged in a single or divided container.

The primers can be in any suitable condition, including in solution, dried, freeze dried, at room temperature, on wet ice, and on dry ice. Additional components may be included in the kits, for example other reagents for performing the monitoring or assessing with the primers. Additional components may include a polymerase for amplification, reagents for preparing template from cancer cells, normal cells, or body fluids, control primers, control templates, labeled or unlabelled deoxyribonucleotides.

In order to identify or confirm a rearrangement in tumor DNA, tumor sequences can be compared to a reference sequence, for example in a database, or to a sequence from normal DNA of the same or a related individual. Two mate-paired tags or two fragment ends that map to different locations on a chromosome or to different chromosomes or to differently oriented sequences on the same chromosome indicate a rearrangement. The comparison can be done in silico or in vitro.

Breakpoints in a rearrangement are places where two sequences are joined in a tumor DNA that are not joined in normal or reference DNA. Thus the breakpoint refers to an inferred break that occurred in order to join the sequences that are found in the tumor DNA. Breakpoints are also referred to as boundaries of a rearrangement. Normal DNA may be obtained from lymphocytes or a buccal swab, for example. In cases where the subject has a diagnosed tumor, normal DNA can be obtained from any non-tumor tissue, including a matched tissue from the same organ.

The breakpoints which are of interest in the present methods are those which are not known to be associated with or causative of leukemia, lymphoma, sarcoma, or prostate cancers. The breakpoints which are associated with or causative of those cancers typically occur in a high proportion of such tumors, often between the same or a limited number of genes or gene loci. The rearrangements used in the present methods are more idiosyncratic, occurring between the same genes or gene loci in less than 1%, less than 0.1%, or less than 0.01% of the patients with the same type of tumor.

Assays using tumor-specific primers can be used for a variety of purposes. For example, patients can be monitored over time to see if a tumor is in remission or is progressing. The assay can be used before, during, and/or after a therapy regimen. The assay can be used to assess surgical efficacy. Tumor margins can be assessed to guide the extent of surgical resection. The assay can be used to monitor for relapse or recurrence.

Using the tumor rearrangement-specific primers to conduct assays, one can obtain qualitative or quantitative results. The quantitative results can be absolute amounts or relative amounts, for example, compared to a non-rearranged sequence on the same or a different chromosome. Assays can be conducted using the rearrangement-specific primers and tissues or body fluids from a subject. Suitable body fluids include whole blood, serum, and plasma, which are collectively referred to as blood. Other body fluids which may be used are saliva, sputum, and stool, for example. One or more pairs of primers can be used to amplify and assay for one or more tumor-specific rearrangements in a single patient. Using a panel of rearrangements markers may mitigate against any possible loss of marker during tumor growth and progression.

The results shown below in the Examples demonstrate that massively parallel sequencing can be used to develop personalized biomarkers based on somatic rearrangements. We were able to identify tumor-specific markers in each of the six breast and colorectal cancer cases analyzed. Moreover, we demonstrated that the identified breakpoints can be used to detect tumor DNA in the presence of large quantities of normal DNA and in patient plasma. These results highlight the sensitivity and specificity of the approach and suggest broad clinical utility of the methods disclosed here, collectively referred to as PARE.

Virtually all tumors of clinical consequence are thought to have rearranged DNA sequences resulting from translocations and copy number alterations and these sequences are not present in normal human plasma or non-tumor tissues. A recent genome-wide analysis of 24 breast cancers showed that all analyzed samples contained at least one genomic rearrangement that could be detected by next generation sequencing (24). From a technical perspective, PARE-derived clinical assays should have no false positives: the PCR amplification of aberrant fusions of DNA sequences that are normally thousands of base pairs apart or on different chromosomes should not occur using non-tumor DNA as a template. In contrast, approaches that rely on monitoring of residual disease by analysis of somatic single base alterations in specific genes are limited by polymerase error rates at the bases of interest (25). The PCR process generates background single base mutations that are identical to bona fide mutations, but does not generate false-positive rearrangements with carefully chosen primers. Because of the higher signal-to-noise ratio thereby obtained, PARE theoretically permits more sensitive monitoring of tumor burden.

The PARE approach, however, is not without limitations. Although somatic alterations in oncogenes and tumor suppressor genes persist throughout the clonal evolution of a tumor, it is conceivable that some rearranged sequences could be lost during tumor progression. The identification of several PARE biomarkers, each specific for different chromosomal regions, would mitigate this concern, as it is unlikely that all such markers would be lost in any particular patient. Another limitation is the cost of identifying a patient-specific alteration. In this prototype study, we obtained an average of 194.7 million reads per patient, resulting in ~200 tags in each 3 kb bin. The current cost for such an assay is $5,000, which is expensive for general clinical use. This cost is a consequence of the high physical coverage and the inefficiencies associated with stringent mapping of 25 bp sequence data to the human genome. As read quality and length continue to improve, less stringent mapping criteria and lower physical coverage will permit analyses similar to those in this study but with substantially less sequencing effort. Moreover, the cost of massively parallel sequencing, which has decreased substantially over the last two years, continues to spiral downwards. Finally, there are clinical settings where the fraction of any DNA from tumors, including rearranged sequences, in the patient plasma is exceedingly small and undetectable. To be detectable by PARE, there must be at least one rearrangement template molecule in the plasma sample analyzed. When disease-burden is this light, PARE may yield false negative results. Larger studies will be needed to confirm particular clinical uses of PARE and its prognostic capabilities.

Despite these caveats, there are numerous potential applications of PARE. These include the more accurate identification of surgical margins free of tumor and the analysis of regional lymph nodes as well as the measurement of circulating tumor DNA following surgery, radiation, or chemotherapy. Short term monitoring of circulating tumor DNA may be particularly useful in the testing of new drugs, as it could provide an earlier indication of efficacy than possible through conventional diagnostic methods such as CT scanning. Given current enthusiasm for the personalized management of cancer patients, PARE affords a timely method for uniquely sensitive and specific tumor monitoring.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Materials and Methods

Clinical Samples and Cell Lines

DNA samples were obtained from early passage xenografts and cell lines of breast and colorectal cancers as described (26). Normal DNA samples were obtained from matched normal tissue. Plasma samples were collected from colorectal cancer patients Hx402 and Hx403 and from an unrelated normal control. All samples were obtained in accordance with the Health Insurance Portability and Accountability Act (HIPAA).

Digital Karyotyping and Illumina BeadChip Arrays

A Digital Karyotyping library for colorectal cancer cell line Co84C was constructed as previously described (6). In summary, 17 bp genomic DNA tags were generated using the NlaIII and SacI restriction enzymes. The experimental tags obtained were concatenated, cloned and sequenced. Previously described software was used to extract the experimental tags from the sequencing data. The sequences of the experimental tags were compared to the predicted virtual tags extracted from the human genome reference sequence. Amplifications were identified using sliding windows of variable sizes and windows with tag density ratios ≥6 were considered to represent amplified regions.

The Illumina Infinium II Whole Genome Genotyping Assay employing the BeadChip platform was used to analyze the colorectal cancer cell line Co84C at 317 k SNP loci from the Human HapMap collection. This assay is a two step procedure; first the sample is hybridized to a 50 nucleotide oligo, then the SNP position is interrogated by a two-color fluorescent single base extension. Image files and data normalization were processed as previously described (10). Amplifications were defined as regions having at least one SNP with a Log R ratio ≥1.4, at least one in ten SNPs with a Log R ratio ≥1, and an average Log R ratio of the entire region of ≥0.9.

SOLiD Library Preparation and Sequencing

Mate-pair libraries were generated for the SOLiD platform as described (15). In brief, genomic DNA was sheared into ~1.4 kb fragments and used as template in emulsion PCR. Fragments were coupled to beads via an adapter sequence and clonally amplified. A 3' modification of the DNA fragments allowed for covalent attachment to a slide. Sequencing primers hybridized to the adapter sequence and four fluorescently labeled di-base probes were used in ligation-based sequencing. Each nucleotide is sequenced twice in two different ligation reactions, resulting in two base encoding which has been shown to reduce sequencing artifacts.

Sequence data was mapped to the human genome reference sequence (hg18) using the Corona SOLiD software pipeline. All 25 bp tags (for both individual tag and mate-paired tag analyses) were required to match the reference genome uniquely and without mismatches.

Analysis of Single Tags for Copy Number Alterations

The SOLiD tags were filtered and the remaining tags were grouped by genomic position in non-overlapping 3 kb bins. A tag density ratio was calculated for each bin by dividing the number of tags observed in the bin by the average number of tags expected to be in each bin (based on the total number of tags obtained for chromosomes 1-22 for each library divided by 849,434 total bins). The tag density ratio thereby allowed a normalized comparison between libraries containing different numbers of total tags. A control group of SOLiD libraries made from the four matched normal samples from Table 1 and two itional normal samples (CEPH sample NA07357 and NA18507 used to define areas of germline copy number variation or which contained a large fraction of repeated or low complexity sequences. Any bin where at least 2 of the normal libraries had a tag density ratio of <0.25 or >1.75 was removed from further analysis.

Homozygous deletions were identified as three or more consecutive bins with tag ratios <0.25 and at least one bin with a tag ratio <0.005. Amplifications were identified as three or more consecutive bins with tag ratios >2.5 and at least one bin with a tag ratio >6. Single copy gains and losses were identified through visual inspection of tag density data for each sample.

Analysis of Mate-Paired Tags

Mate-paired tags mapping the reference genome uniquely and without mismatches were analyzed for aberrant mate-pair spacing, orientation and ordering and categorized in 13 three letter data formats (27). Mate pairs from the same chromosome that map at appropriate distances (~1.4 kb) and in the appropriate orientation and ordering are categorized as AAA. Mate pairs mapping to different chromosomes are categorized as C. For the analysis of translocations of the PARE approach, we focused on C mate pairs, while for analysis of rearrangements adjacent to copy number alterations, we chose all non-AAA (including C**) mate pairs for further analysis.

PARE Identification and Confirmation of Candidate Rearrangements

To identify candidate translocations, we grouped C** mate pair tags in 1 kb bins and looked for bin-pairs which were observed ≥5 times in the tumor sample but which were not observed in matched normal sample. For identification of candidate rearrangements associated with copy number alterations, we analyzed the 10 kb boundary regions of amplifications, homozygous deletions, or lower copy gains and losses for neighboring non-AAA tags observed >2 times in the tumor but not matched normal sample. In the case of Hx402 and Hx403 the analysis of rearrangements adjacent to copy number alterations was performed in the absence of SOLiD libraries from normal tissue.

Mate pair tag sequences associated with a candidate rearrangement were used as target sequences for primer design using with Primer3 (28). When primers could not be designed from tag sequences alone, adjacent genomic sequence up to 100 bp was used for primer design. Importantly, the observed rearranged tag ordering and orientation was used for Primer3 queries. Primers were used for PCR on tumor and matched normal samples as previously described (26). The candidate rearrangement was confirmed if a PCR product of the expected size was seen in the tumor, but not the matched normal sample. Sanger sequencing of PCR products was used to identify sequence breakpoint in a subset of cases.

Detection of PARE Biomarker in Human Plasma

To determine the sensitivity of rearranged biomarkers in the presence of normal DNA, serial dilutions of tumor:normal DNA mixtures were used as templates for PCR using primers for the chromosome 4/8 translocation in Hx402. The tumor DNA dilution began at 1:125 tumor:normal and continued as a one-in-five serial dilution until reaching 1:390,625 tumor:normal mixture. PCR was performed for each of the six tumor:normal DNA mixtures and for the normal DNA control, using translocation specific primers as well as control primers from chromosome 3.

One ml of human plasma samples were obtained from patients Hx402 and Hx403 and from a control individual and DNA was purified as described (29). Whole genome amplification of plasma DNA was performed by ligation of adaptor sequences and PCR amplification with universal primers from the Illumina Genomic DNA Sample Prep Kit. Primers designed to amplify <200 bp fragments spanning each PARE rearrangement were used in PCR from total plasma DNA using patient or control samples. Digital PCR of plasma DNA dilutions from patient Hx402 using rearrangement specific and control primers were used to quantitate the fraction mutated DNA molecules.

Example 2

Description of the Approach

The PARE approach, shown schematically in FIG. 1, in one embodiment employs the identification of patient-specific rearrangements in tumor samples. To determine the feasibility of identifying such alterations using next generation sequencing approaches, we initially analyzed four tumor samples (two colon and two breast tumors) and their matched normal tissue samples using the Applied Biosystems SOLiD System (Table 1). Genomic DNA from each sample was purified, sheared and used to generate libraries with mate-paired tags ~1.4 kb apart. Libraries were digitally amplified by emulsion polymerase chain reaction (PCR) on magnetic beads (21) and 25 bp mate-paired tags were sequenced using the sequencing-by-ligation approach (15, 22). An average of 198.1 million 25 bp reads were obtained for each sample where each read aligned perfectly and was uniquely localized in the reference human genome (hg18), resulting in 4.95 Gb mappable sequence per sample. An average of 40 million mate-paired reads where both tags were perfectly mapped to the reference human genome were obtained for each sample. The total amount of genome base-pairs covered by the mate-paired analysis (i.e. distance between mate-paired tags×number of mate-paired tags) was 53.6 Gb per sample, or a 18-fold physical coverage of the human genome.

TABLE 1

Summary of mate-paired tag libraries

| | | Single tag analyses | | | Mate-paired tag analyses | | | |
|---|---|---|---|---|---|---|---|---|
| Samples | Number of beads* | Number of tags matching human genome | Total bases sequenced (bp) | Expected coverage per 3 kb bin | Number of mate-paired tags matching human genome | Distance between mate-paired tags (bp) | Total physical coverage by mate-paired tags (bp) | Expected genome coverage |
| Colon Cancer | | | | | | | | |
| Co108 tumor | 526,209,780 | 121,527,707 | 3,038,192,675 | 122 | 21,899,809 | 1,371 | 30,024,693,714 | 10.0 |
| Co108 normal | 328,599,033 | 86,032,253 | 2,150,806,325 | 86 | 11,694,361 | 1,254 | 14,665,530,804 | 4.9 |
| Co84 tumor | 677,137,128 | 256,065,437 | 6,401,635,925 | 256 | 58,678,410 | 1,488 | 87,292,060,006 | 29.1 |
| Co84 normal | 486,663,520 | 218,280,146 | 5,457,003,650 | 218 | 59,019,031 | 1,384 | 81,690,396,379 | 27.2 |
| Hx402 tumor | 523,745,015 | 198,342,749 | 4,958,568,725 | 198 | 43,457,431 | 1,629 | 70,789,547,653 | 23.6 |
| Hx403 tumor | 475,658,760 | 164,061,938 | 4,101,548,450 | 164 | 37,123,395 | 1,705 | 63,295,388,475 | 21.1 |
| Breast cancer | | | | | | | | |
| B7 tumor | 840,979,999 | 281,027,274 | 7,025,681,850 | 281 | 27,548,989 | 1,220 | 33,604,662,404 | 11.2 |
| B7 normal | 705,704,265 | 253,482,262 | 6,337,056,550 | 253 | 57,878,644 | 1,404 | 81,271,654,770 | 27.1 |
| B5 tumor | 444,249,217 | 147,612,941 | 3,690,323,525 | 148 | 29,961,045 | 1,193 | 35,730,144,651 | 11.9 |
| B5 normal | 549,237,156 | 220,669,795 | 5,516,744,875 | 221 | 53,611,974 | 1,205 | 64,591,276,025 | 21.5 |

*Number of beads corresponds to the number of magnetic beads containing clonally amplified DNA fragments and represents the maximal number of raw sequnece reads for each run.

Example 3

Identification of Somatic Rearrangements

Figure 5:
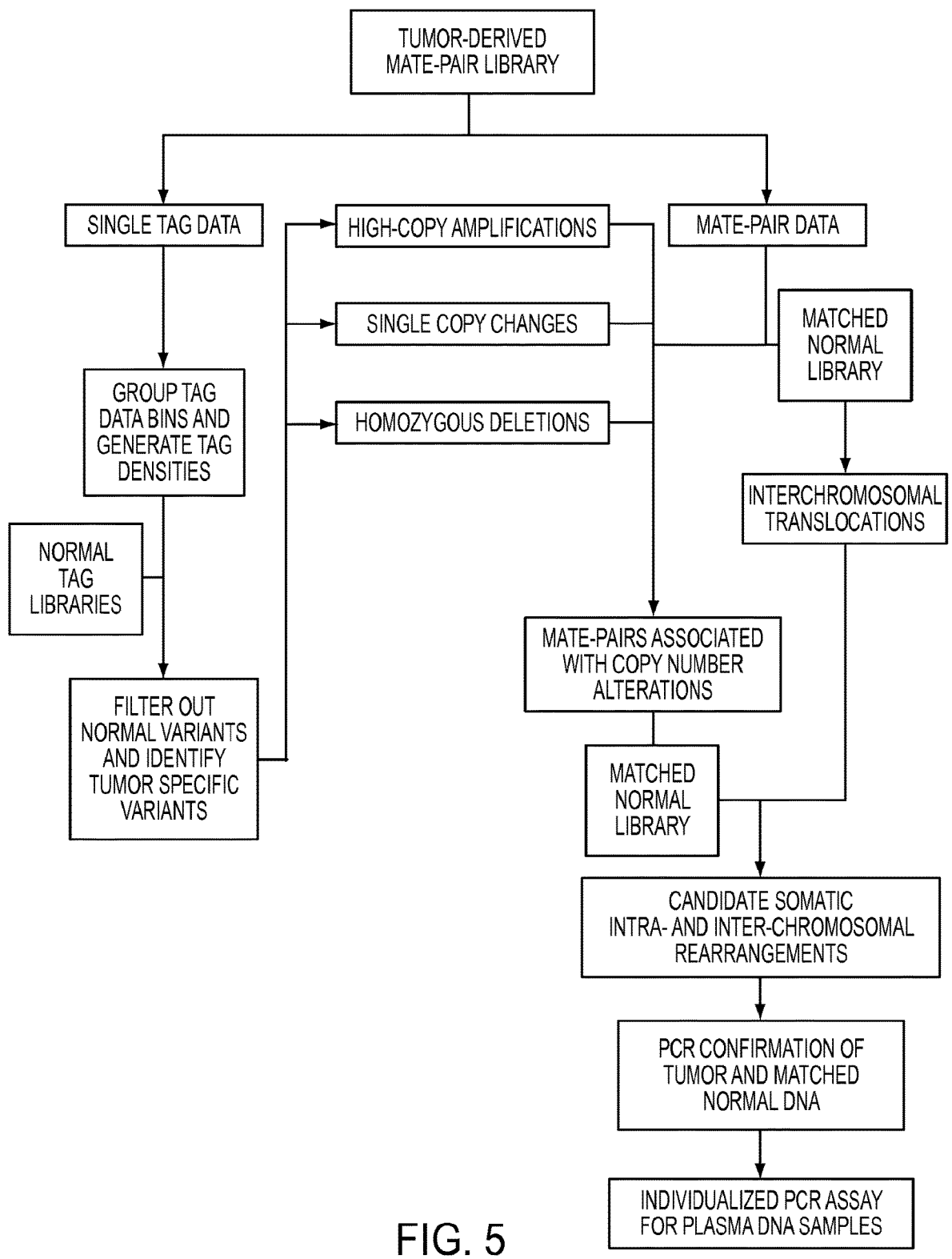
FIG. 5 (Figure S1.) Flow chart of approach used to identify rearranged sequences FIG. 6 (Figure S2.) Comparison of Digital Karyotyping, Illumina SNP array, and SOLiD sequencing results on chromosome 8.

Two methods were used to identify somatic rearrangements from these data (FIG. 5). The first approach involved searching for tags whose mate-pairs were derived from different chromosomes (interchromosomal rearrangements). The high physical coverage of breakpoints provided by the ~40 million mate-paired sequences per sample (Table 1) suggested that a large fraction of such translocations could be identified. End sequences from such mate-paired tags were grouped into 1 kb bins and those bin pairs that were observed at least 5 times were analyzed further. The requirement for ≥5 occurrences minimized the chance that the presumptive fusion sequences represent incorrect mapping to the reference genome or artifacts of library construction. Comparison with SOLiD libraries made from the matched normal samples reduced the possibility that the fusion sequences represented rare germline variants rather than somatic events.

Figure 6:
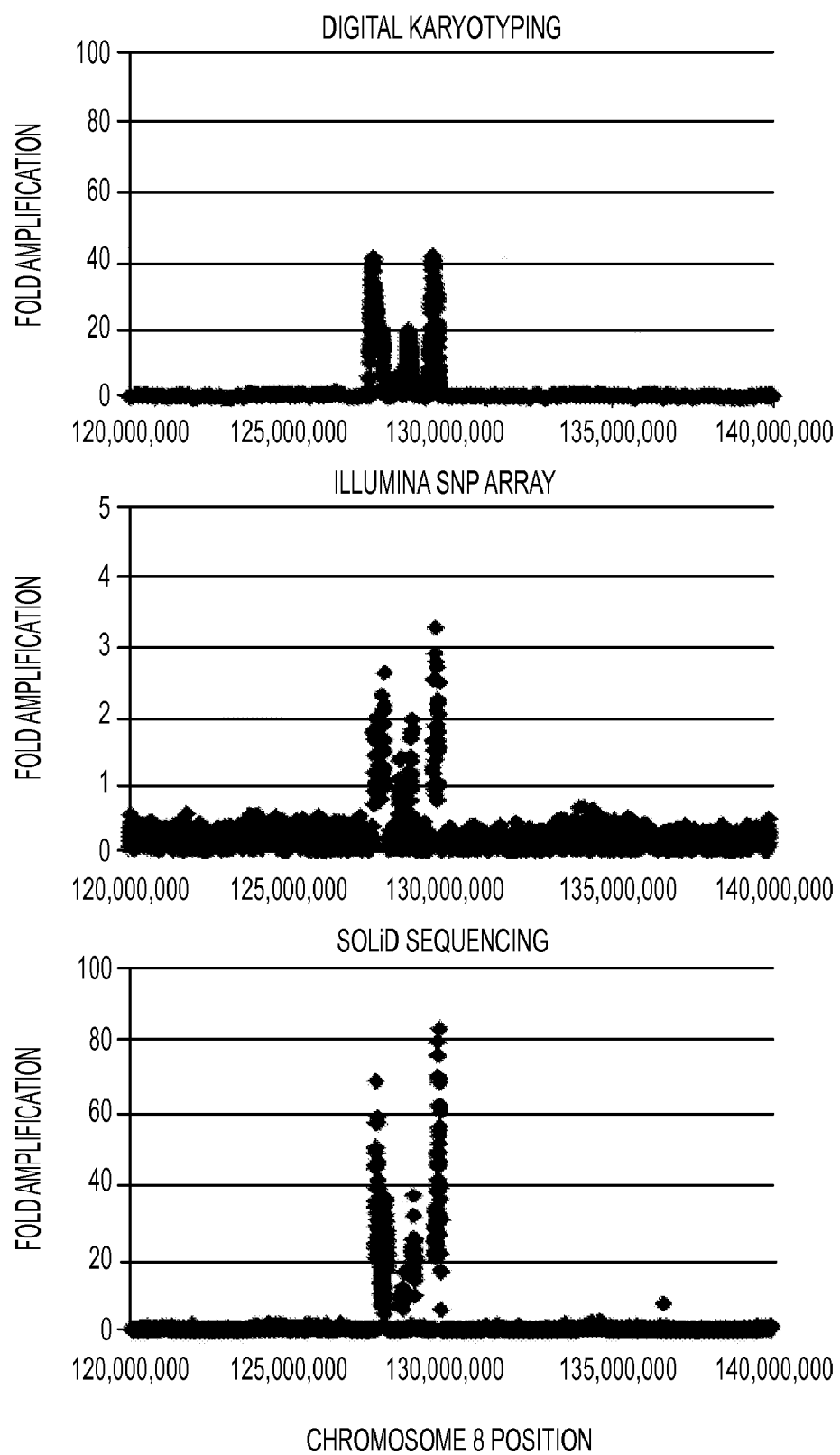

The second approach combined mate-paired tag data with copy number alterations identified by analyses of individual 25 bp tags. Tumor-specific copy number alterations are often associated with de novo rearrangements (23) and the boundaries of such alterations would be expected to contain novel junctions not present in the human genome. To identify somatic copy number gains, losses, high-amplitude amplifications and homozygous deletions, tags were grouped into non-overlapping 3 kb bins. Normalized tag densities, defined as the number of tags per bin divided by average number of tags per bin, were determined for all 3 kb bins in each sample. Bins that displayed tag density ratios >1.75 or <0.25 in two or more normal tissue samples (corresponding to <6% of all bins) were discarded from the analysis. This eliminated confounding regions of common germline copy number variation and resulted in 892,567 bins that were analyzed in each tumor sample. Comparison of 256 million reads from colorectal tumor sample Co84 with Illumina arrays containing ~1 million SNP probes and with a ~1 million Digital Karyotyping (DK) tag library obtained with Sanger sequencing showed high concordance for copy number alterations among the three platforms (FIG. 6 and Table S1). With the higher resolution afforded by the SOLiD data, we were able to identify additional copy number changes not detected with the other methods (Table S2). Boundary regions of copy number alteration were analyzed to identify mate-paired tags corresponding to rearranged DNA sequences. These included fusion of DNA sequences that have inappropriate spacing, order or orientation on the same chromosome (intrachromosomal rearrangements) or inappropriate joining of sequences from different chromosomes (interchromosomal rearrangements).

TABLE S1

Comparison of SOLiD sequencing, Illumina SNP arrays, and Digital Karyotyping for analysis of copy number alterations

| | | | Digital Karyotyping | | | | Illumina SNP Arrays | | | |
|---|---|---|---|---|---|---|---|---|---|---|
| | Tumor Sample | Chr | Left Boundary | Right Boundary | Size (bp) | Tag Density Ratio* | Left Boundary | Right Boundary | Size (bp) | Log R Ratio* |
| Amplification | Co84C | 6 | 41,273,307 | 43,008,812 | 1,735,506 | 9.1 | 41,419,345 | 42,485,546 | 1,066,202 | 1.9 |
| Amplification | Co84C | 8 | 127,618,526 | 128,009,287 | 390,762 | 19.2 | 127,621,008 | 127,995,012 | 374,005 | 2.7 |
| Amplification | Co84C | 8 | 128,750,189 | 128,857,861 | 107,673 | 8.3 | 128,750,181 | 128,848,183 | 98,003 | 2.0 |
| Amplification | Co84C | 8 | 129,473,672 | 129,667,129 | 193,458 | 13.8 | 129,472,209 | 129,677,099 | 204,891 | 3.4 |
| Amplification | Co84C | 11 | 34,337,207 | 35,266,401 | 929,195 | 33.0 | 34,359,268 | 35,265,359 | 906,092 | 3.0 |
| Amplification | Co84C | 13 | 109,096,557 | 109,553,930 | 457,374 | 9.2 | 109,108,212 | 109,557,712 | 449,501 | 2.3 |
| Amplification | Co84C | 15 | 88,545,070 | 89,258,106 | 713,037 | 26.2 | 88,561,995 | 89,253,599 | 691,605 | 3.6 |
| Amplification | Co84C | 19 | 34,570,450 | 34,641,949 | 71,500 | 7.9 | 34,561,976 | 34,641,548 | 79,573 | 2.2 |
| Amplification | Co84C | 19 | 34,956,853 | 35,344,522 | 387,670 | 14.3 | 34,966,463 | 35,321,409 | 354,947 | 2.6 |
| Amplification | Co84C | 19 | 36,274,262 | 36,388,331 | 114,070 | 6.2 | 36,281,540 | 36,385,232 | 103,693 | 2.5 |
| Amplification | Co84C | 19 | 54,500,237 | 54,643,655 | 143,419 | 8.4 | 54,520,709 | 54,622,533 | 101,825 | 2.1 |

| | | | SOLiD sequencing | | | |
|---|---|---|---|---|---|---|
| | Tumor Sample | Chr | Left Boundary | Right Boundary | Size (bp) | Tag Density Ratio* |
| Amplification | Co84C | 6 | 41,418,000 | 42,537,000 | 1,119,001 | 16.4 |
| Amplification | Co84C | 8 | 127,617,000 | 128,010,000 | 393,001 | 150.0 |
| Amplification | Co84C | 8 | 128,748,000 | 128,859,000 | 111,001 | 43.1 |
| Amplification | Co84C | 8 | 129,471,000 | 129,678,000 | 207,001 | 116.6 |
| Amplification | Co84C | 11 | 34,338,000 | 35,268,000 | 930,001 | 91.2 |
| Amplification | Co84C | 13 | 109,107,000 | 109,557,000 | 450,001 | 33.6 |
| Amplification | Co84C | 15 | 88,542,000 | 88,953,000 | 411,001 | 93.2 |
| | | | 88,983,000 | 89,118,000 | 135,001 | 32.8 |
| | | | 89,133,000 | 89,166,000 | 33,001 | 84.8 |
| | | | 89,208,000 | 89,256,000 | 48,001 | 50.3 |
| Amplification | Co84C | 19 | 34,548,000 | 34,641,000 | 93,001 | 33.9 |
| Amplification | Co84C | 19 | 34,956,000 | 35,346,000 | 390,001 | 36.8 |
| Amplification | Co84C | 19 | 36,273,000 | 36,396,000 | 123,001 | 21.2 |
| Amplification | Co84C | 19 | 54,498,000 | 54,636,000 | 138,001 | 41.8 |

*Values for Tag Density Ratios and Log R Ratios represent observed maximum values for amplifications.

TABLE S2

Putative copy number alterations identified by SOLiD sequencing in Co84 that were not identified by Illumina SNP arrays or Digital Karyotyping

| Alteration Type | Chromosome | Left Boundary | Right Boundary | Size (bp) | Tag Density Ratio* |
|---|---|---|---|---|---|
| Homozygous deletion | 1 | 83,388,000 | 83,532,000 | 144,001 | 0.0 |
| Amplification | 1 | 151,188,000 | 151,194,000 | 6,001 | 11.2 |
| Amplification | 1 | 159,393,000 | 159,414,000 | 21,001 | 9.7 |
| Amplification | 1 | 172,101,000 | 172,107,000 | 6,001 | 18.1 |
| Amplification | 1 | 179,910,000 | 179,916,000 | 6,001 | 17.4 |
| Amplification | 1 | 200,238,000 | 200,256,000 | 18,001 | 9.6 |
| Amplification | 1 | 204,168,000 | 204,186,000 | 18,001 | 13.2 |
| Homozygous deletion | 4 | 9,804,000 | 9,813,000 | 9,001 | 0.0 |
| Homozygous deletion | 4 | 69,066,000 | 69,171,000 | 105,001 | 0.0 |
| Homozygous deletion | 4 | 147,138,000 | 147,147,000 | 9,001 | 0.0 |
| Amplification | 5 | 31,749,000 | 31,755,000 | 6,001 | 12.3 |
| Homozygous deletion | 5 | 114,279,000 | 114,288,000 | 9,001 | 0.0 |
| Homozygous deletion | 7 | 38,358,000 | 38,364,000 | 6,001 | 0.0 |
| Amplification | 8 | 145,698,000 | 145,725,000 | 27,001 | 11.5 |
| Homozygous deletion | 10 | 66,978,000 | 66,984,000 | 6,001 | 0.0 |
| Homozygous deletion | 13 | 108,681,000 | 108,687,000 | 6,001 | 0.0 |
| Amplification | 13 | 110,139,000 | 110,157,000 | 18,001 | 22.5 |
| Homozygous deletion | 16 | 54,357,000 | 54,378,000 | 21,001 | 0.0 |

TABLE S2-continued

Putative copy number alterations identified by SOLiD sequencing in Co84 that were not identified by Illumina SNP arrays or Digital Karyotyping

| Alteration Type | Chromo-some | Left Boundary | Right Boundary | Size (bp) | Tag Density Ratio* |
|---|---|---|---|---|---|
| Homozygous deletion | 16 | 59,112,000 | 59,130,000 | 18,001 | 0.0 |
| Amplification | 17 | 76,467,000 | 76,482,000 | 15,001 | 17.8 |
| Homozygous deletion | 18 | 14,268,000 | 14,289,000 | 21,001 | 0.0 |
| Amplification | 19 | 50,271,000 | 50,277,000 | 6,001 | 9.3 |
| Amplification | 20 | 25,404,000 | 25,428,000 | 24,001 | 13.1 |
| Homozygous deletion | X | 49,050,000 | 49,059,000 | 9,001 | 0.0 |
| Homozygous deletion | X | 121,650,000 | 121,734,000 | 84,001 | 0.0 |

*Values for Tag Density Ratios represent observed maximum values for amplifications.

Figures 2A, 2B:
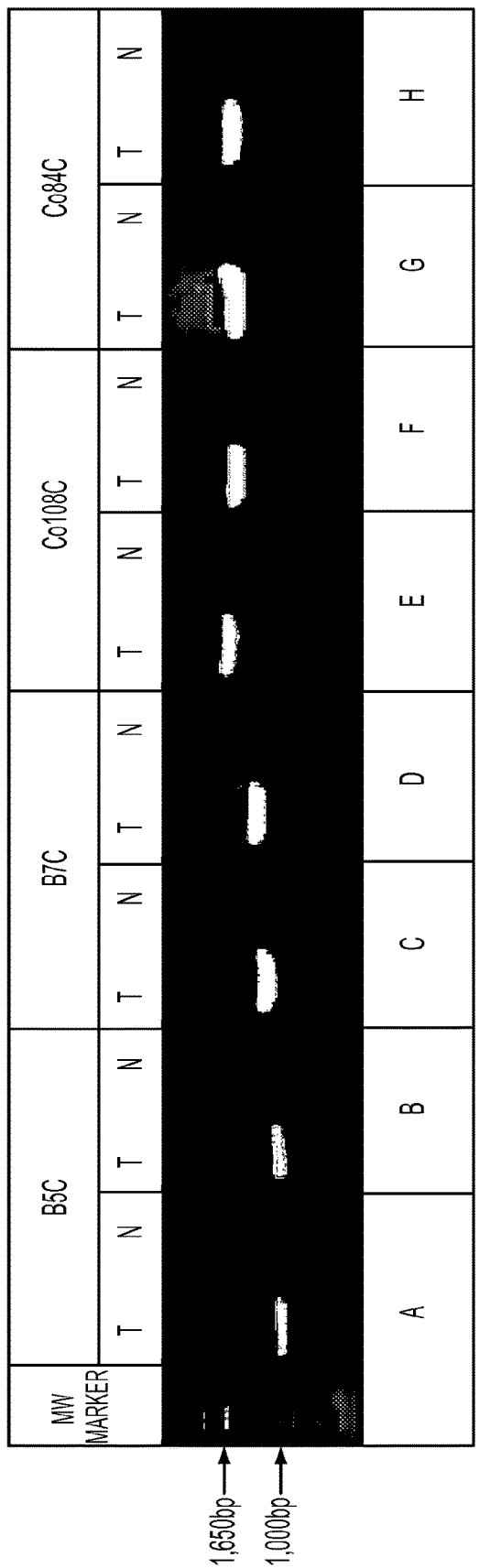
FIGS. 2A and 2B. Detection of tumor-specific rearrangements in breast and colorectal cancers. Two representative rearrangements are shown for each tumor sample. PCR amplification across breakpoint regions is indicated in (FIG. 2A) and the genomic coordinates for a representative mate-pair of each rearrangement are listed in (FIG. 2B).

Through these two approaches, we identified 57 regions containing putative somatic rearrangements, with an average of 14 rearrangements per sample (Table 2). Of these, an average of seven represented interchromosomal rearrangements and seven represented intrachromosomal rearrangements. For confirmation, we designed primers to 42 of the paired-end regions and used them for PCR spanning the putative breakpoints. Thirty-five of these (83%) yielded PCR products of the expected size in the tumor samples but not in the normal samples (FIG. 2A-2B, Table S3). Sanger sequencing of seven PCR products confirmed the rearrangements in all cases tested. Though there was variation in the number of detected alterations per sample (range 7 to 21), all four tumor samples were found to have at least 4 bona fide somatic rearrangements through this approach.

TABLE 2

Summary of rearrangements idenitified in tumor samples

| Sample | Rearrangement type | | Total rear-range-ments | Tested rear-range-ments | Confirmed somatic rearrange-ments |
|---|---|---|---|---|---|
| | Intra-chromo-somal | Inter-chromo-somal | | | |
| Tumor and normal libraries | | | | | |
| B5 | 7 | 4 | 11 | 7 | 5 (71%) |
| B7 | 17 | 4 | 21 | 16 | 15 (94%) |
| Co84 | 0 | 7 | 7 | 6 | 4 (67%) |
| Co108 | 6 | 12 | 18 | 13 | 11 (85%) |
| Tumor libraries | | | | | |
| Hx402 | 7 | 2 | 9 | 9 | 4 (44%) |
| Hx403 | 17 | 0 | 17 | 12 | 7 (58%) |

TABLE S3

Confirmed somatic rearrangements in breast and colorectal cancer samples*

| Sample | Chromo-some | Position | Chromo-some | Position | Type | Primer 1 | Primer 2 |
|---|---|---|---|---|---|---|---|
| B5C | 3 | 52,638,626 | 3 | 52,573,088 | AAC | AAGTTTTTCAAGCTTTACCTGAAGT | TATATTGGAAGAATAGAAATGAATGG |
| B5C | 4 | 93,109,700 | 4 | -93,105,085 | BAC | AGCCAAGTGCAATTCTCCAG | GCACACTGTTTGCAGGAATG |
| B5C | 11 | 57,713,780 | 8 | -48,889,516 | C** | GCCACCTTTCTTTCTTTCTGA | AAGCTTTGTTTGGTTGTTCTCA |
| B5C | 18 | 19,141,985 | 20 | -29,591,944 | C** | TGGCTTTCAAAACCCACTG | TCCTTTCTGCCCATTAGGG |
| B5C | 22 | 48,743,603 | 2 | -104,047,142 | C** | TCATGGTTTATCCACGGTGT | CACACCGCATTCACACAAAC |
| B7C | 1 | -96,237,189 | 7 | 65,542,257 | C** | TCAAAACAGAAAGCATTAGGC | CGCATCCAAAGTATTAATAGCAA |
| B7C | 2 | 197,426,606 | 2 | 113,761,988 | AAC | AACTCCTCCCACCTCAAAATC | CCAAATTGCCTGCTTAAGAGAT |

TABLE S3-continued

Confirmed somatic rearrangements in breast and colorectal cancer samples*

| Sample | Chromosome | Position | Chromosome | Position | Type | Primer 1 | Primer 2 |
|---|---|---|---|---|---|---|---|
| B7C | 2 | -32,084,286 | 3 | 185,241,029 | C** | TGCTACCAATACTTCCCACTTG | TACCGTCCTCCAGGCATGT |
| B7C | 2 | 114,604,628 | 18 | 53,562,784 | C** | GGAGAAAACCCTGGTTATTTTTA | TCCCTCATCAGAGCAAATCA |
| B7C | 3 | -115,579,348 | 3 | -115,651,310 | AAC | AAATTGGGAAGGATCATACTGAC | TCTGAACATGCCTGATCTCATC |
| B7C | 4 | 785,983 | 4 | 733,804 | AAC | CTGAACTCCTGGGCTGAA | TTGCTAAGTGATGCTACCTGTG |
| B7C | 5 | 107,405,959 | 5 | 107,231,803 | AAC | CCTGGCCCCTTAGGTAAGAT | TGAAGAATCCTTCTAGTGATGGAA |
| B7C | 5 | 38,284,430 | 10 | -44,715,202 | C** | TGCAGCTTTTCTCTGTCTTCA | CTGCCAGTCCAAACTGGTG |
| B7C | 6 | 106,401,376 | 6 | 90,853,847 | AAC | TGCTGTTTCAAATTCCTACAG | TGAAATTAGGACCTGGAGCACTC |
| B7C | 6 | 101,933,981 | 6 | 102,444,426 | ABC | GCCAGGTAACATGCTCACTTT | GATGCAGGAAGTTGACAGCA |
| B7C | 9 | 22,003,033 | 9 | 21,761,298 | AAC | GGGCTAAGCTTAAGAGTCTGG | GCCATGTGCAAGTCAAGAAG |
| B7C | 11 | -6,436,033 | 11 | -6,519,897 | AAC | TCTGCCGGCATACTGGAC | TAAGGGCGATGTGAACAAGG |
| B7C | 12 | 65,950,588 | 12 | 65,923,399 | AAC | GCCCTATTTTCAGAGAAAGTGGTA | AACATCTCTTCCTTTTGAAGATCC |
| B7C | 13 | 60,438,525 | 13 | 52,159,979 | AAC | AATTTGCTCTCATCGTATTGTGT | AGCTGAATCAAAATTTCCAATG |
| B7C | X | 31,583,118 | X | 31,179,704 | AAC | CTGAATCTCTTTCCAGCAAAAT | AATGGGTTAAGCAGTTTAGGG |
| Co108C | 2 | 191,184,628 | 5 | -104,930,827 | C** | TAGCATGCACCACTTTAGGC | AAAGGTTAAAGGACTGTTTTAAGTTG |
| Co108C | 2 | 78,849,963 | 6 | -13,299,323 | C** | GGTTCTGGAGGGTTGGAGA | GTTAAGATCAACATTTTTGTTTCAAG |
| Co108C | 2 | -7,268,710 | 6 | 13,299,385 | C** | TATGCCACCATCGCTTAGGT | TCCCAGTGCAATAAAACCAA |
| Co108C | 2 | -141,266,016 | 13 | 96,916,170 | C** | GGTGTTCTCTCTCCCATACCA | CGATCTATACACCACCCCACA |
| Co108C | 3 | -60,400,269 | 3 | -60,437,489 | AAC | TGCTTTTAGTTTTGGGTACGG | GCTGATTGTTTATACCCAGTGC |
| Co108C | 3 | -60,365,933 | 3 | -60,498,861 | AAC | ATCCTCGGACTGGACTGAGA | AACCCCATCCTGAAGCTACC |
| Co108C | 3 | 60,573,034 | 3 | 60,472,593 | AAC | GGGTTATCTCAAAAGGGCAGA | GCTCTCAATTTGTGTGATTTGG |
| CoL108C | 4 | 81,934,151 | 15 | 54,039,041 | C** | TGTGTTCCTCTCCTCTTAAGCAT | GACTACAAATGGCCCAGACTC |
| Co108C | 6 | -13,299,291 | 5 | 157,523,537 | C** | ATCCCCACATTCCCAACC | CCCAGCCATATGTTGGTTTA |
| Co108C | 6 | 13,299,271 | 2 | -20,956,947 | C** | GTATTTGTTCATGTTTGTTAGGTGTT | TCAATGGGGAGAGAGAGC |
| Co108C | 13 | 34,581,537 | 10 | 67,756,452 | C** | ACGTGTGTATTGGGGGTAGC | CCAGATGGCTGGGTTAAATAAA |
| Co84C | 8 | 128,442,121 | 19 | 49,144,200 | C** | AGCTAGGTGGAGAATTTGTCG | GGCTTCTGTAGAGTGCACATGA |
| Co94C | 11 | 34,790,251 | 13 | 109,267,462 | C** | AAGGAGATTGGTTATTGTGAAA | CTGCAGGAACTGTCTCATTCTT |
| Co84C | 11 | -34,405,644 | 15 | 88,736,701 | C** | TGCTGAATCATTCTCCCAACT | TGGTGATTCCACTGAGGTGA |
| Co84C | 15 | -89,096,347 | 8 | 127,747,412 | C** | GCATTCTAAAGATGAAGTCCCATT | GGAAACCGTTAGTGGAAAAGTC |

TABLE S3-continued

Confirmed somatic rearrangements in breast and colorectal cancer samples*

| Sample | Chromo-some | Position | Chromo-some | Position | Type | Primer 1 | Primer 2 |
|---|---|---|---|---|---|---|---|
| Hx402x | 8 | 96,971,644 | 4 | 156,043,548 | C** | CAGGTGATATACCAAAGAAAATTAGG | TTTGGGTTCAGTTCTATTTGAAGA |
| Hx402x | 5 | -100,413,406 | 5 | -137,521,052 | AAC | AGTCAACGCCCTAGCATGG | TGGGCATGAGCAAGATATTC |
| Hx402x | 8 | -144,771,376 | 8 | -144,787,051 | AAC | AATCACGTTGGGTGACTGTG | GTGACAGGCTGGGTGTCC |
| Hx402x | 14 | -85,526,541 | 14 | -85,560,400 | AAC | TGAAGGTTGAGTTGCCAGTG | TGTATGAAACATTGTAGAGGCTGT |
| Hx403x | 1 | 119,547,240 | 1 | -119,550,445 | BBC | AGGAGGAAAGCAACACATAGAG | GGTGATTTTCAATGCATATTTCA |
| Hx403x | 5 | -27,160,637 | 5 | 27,150,736 | BBC | AATTACCACAACTCCCAGCAG | CAAAAGATTTCCAAATGCAGGT |
| Hx403x | 11 | 66,674,459 | 11 | 66,662,814 | AAC | TGAATCAGAAAGTCTGGCAGT | CACTTGAGAATCAATGATATGCAG |
| Hx403x | 16 | 6,343,641 | 16 | 6,727,736 | AAC | CCTAGCCCTTTGTTCCCTGT | TTTGTGTACCTAGACATTCATCCAA |
| Hx403x | 16 | 6,574,321 | 16 | 6,759,729 | AAC | GCAGAGAACAGCAGAAAAGTTG | AGCCAAGATCAAGCCACAGA |
| Hx403x | 16 | 26,579,136 | 17 | -26,582,595 | BBC | TTCTCTTTCTCTGCCTTCAGTG | TTGATGATTTAGAAACTCTAGCCTGT |
| Hx403x | 17 | 34,622,352 | 17 | -34,624,284 | BBA | GGCTCCCCTCTCCATTCC | CTGCTGACGTGCTGGTCTT |

*A single representative mate pair is shown for each arrangement. Forward and reverse tags and their genomic coordinates correspond to F3 and R3 SOLiD mate pair tags. The type of rearrangement corresponds to the categories in www3.appliedbiosystems.com (see, cms/groups/mcb_marketing/documents/generaldocuments/cms_058717.pdf). AAC corresponds to mate pairs spanning deletions; codes starting with B denote incorrect strand orientation; codes containing a B at the middle position denote incorrect ordering; and C** corresponds to interchromosomal translocations. Primers 1 and 2 correspond to primers used for confirming tumor-specific rearranged sequences.

Further examination revealed that rearrangements could be readily identified with high confidence even in the absence of data from matched normal DNA by using the copy number and mate-pair coupled approach. Elimination of analysis of the matched normal would reduce the cost and simplify the identification of rearrangements. To test this strategy, two additional tumor samples (Hx402 and Hx403) were then analyzed through the SOLiD approach, but without generation of matching normal DNA libraries. We found that it was possible to identify putative rearrangements resulting in inter- and intrachromosomal rearrangements at the border of copy number variations with high specificity even in the absence of a matched normal library. We were able to identify 11 confirmed somatic alterations (4 and 7 in Hx402 and Hx403, respectively) out of 21 candidate changes tested (Table S3).

Example 4

Development of PARE Biomarkers from Rearranged Sequences

Figure 3:
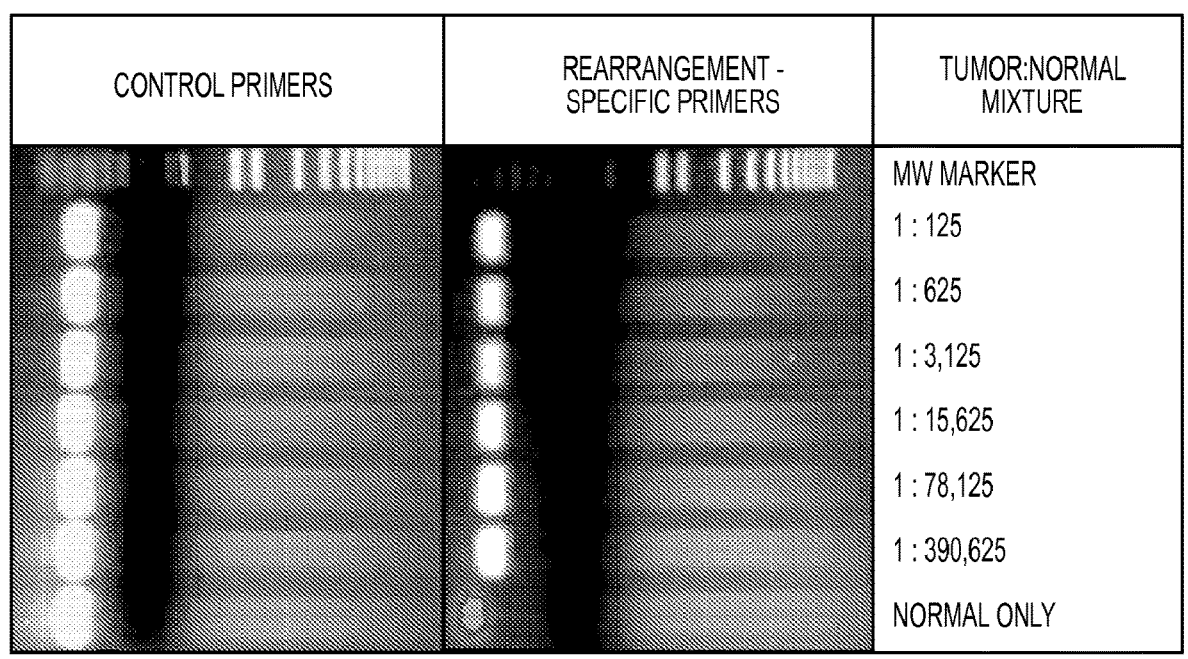
FIG. 3. Detection of tumor specific rearrangements in mixtures of tumor and normal DNA. Decreasing amounts of tumor DNA were mixed with increasing amounts of normal tissue DNA (300 ng total) and were used as template molecules for PCR using chromosomes 4/8 translocation specific primers (top) or chromosome 3 control primers (see Example 1 for additional information).

Each of the rearranged sequences identified through PARE was unique, as no identical rearrangement was found in any of the other five tumor samples. To determine the utility of these rearranged sequences to serve as potential biomarkers, we designed PCR assays to detect them in the presence of increasing amounts of normal DNA. These conditions simulate detection of tumor DNA from patient blood or other bodily fluids where tumor DNA comprises a minority of total DNA. PCR products representing a rearranged region from each of the six dilutions of tumor DNA could be identified, even in mixtures of DNA containing 1 cancer genome equivalent among 390,000 normal genome equivalents (FIG. 3). Furthermore, no background PCR products were discernable when DNA from normal tissues was used as control.

Figure 4A:
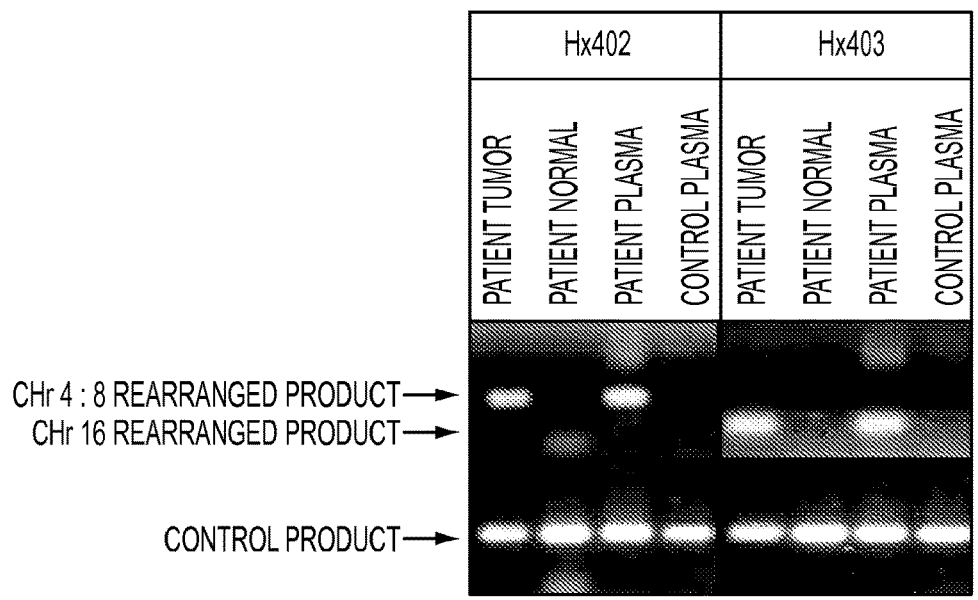
FIG. 4A-4B. Detection of tumor-specific rearrangements in plasma of cancer patients.
Figure 4B:
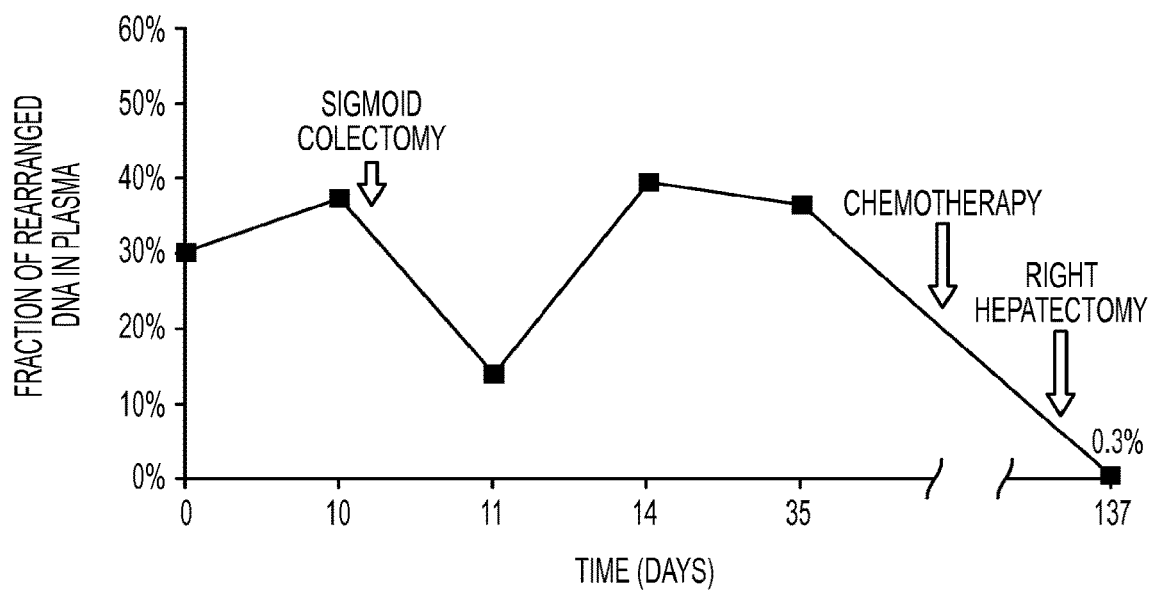

To determine whether the rearranged sequences could actually be detected in clinical samples, we evaluated circulating DNA from plasma samples of patients Hx402 and Hx403. The sample from patient Hx403 was obtained prior to surgery while the samples from patient Hx402 were obtained prior to and after surgery. A chromosome 4:8 translocation associated with an amplification was used in tumor Hx402 and an intrachromosomal rearrangement associated with a homozygous deletion of chromosome 16 was used in tumor Hx403. PCR amplification of plasma DNA using primers spanning the breakpoints produced products of the expected sizes only in the plasma samples from patients with disease and not in plasma from healthy controls (FIG. 4A). Sequencing of the PCR products from plasma DNA identified the identical breakpoints observed in the tumor DNA samples.

Example 5

Detection of PARE Biomarker in Human Plasma

To determine the sensitivity of rearranged biomarkers in the presence of normal DNA, serial dilutions of tumor:normal DNA mixtures were used as templates for PCR using primers for the chromosome 4/8 translocation in Hx402. The tumor DNA dilution began at 1:125 tumor:normal and continued as a one-in-five serial dilution until reaching 1:390,625 tumor:normal mixture. PCR was performed for each of the six tumor:normal DNA mixtures and for the normal DNA control, using translocation specific primers as well as control primers from chromosome 3.

One ml of human plasma samples were obtained from patients Hx402 and Hx403 and from a control individual and DNA was purified as described (29). Whole genome amplification of plasma DNA was performed by ligation of adaptor sequences and PCR amplification with universal primers from the Illumina Genomic DNA Sample Prep Kit.

Primers designed to amplify <200 bp fragments spanning each PARE rearrangement were used in PCR from total plasma DNA using patient or control samples. Digital PCR of plasma DNA dilutions from patient Hx402 using rearrangement specific and control primers were used to quantitate the fraction mutated DNA molecules.

REFERENCES

The disclosure of each reference cited is expressly incorporated herein.

1. C. Lengauer, K. W. Kinzler, B. Vogelstein, Genetic instabilities in human cancers. Nature 396, 643-649 (1998).
2. F. Mitelman, B. Johansson, F. Mertens, The impact of translocations and gene fusions on cancer causation. Nat Rev Cancer 7, 233-245 (2007).
3. D. Pinkel, R. Segraves, D. Sudar, S. Clark, I. Poole, D. Kowbel, C. Collins, W. L. Kuo, C. Chen, Y. Zhai, S. H. Dairkee, B. M. Ljung, J. W. Gray, D. G. Albertson, High resolution analysis of DNA copy number variation using comparative genomic hybridization to microarrays. Nat Genet 20, 207-211. (1998).
4. R. Lucito, J. Healy, J. Alexander, A. Reiner, D. Esposito, M. Chi, L. Rodgers, A. Brady, J. Sebat, J. Troge, J. A. West, S. Rostan, K. C. Nguyen, S. Powers, K. Q. Ye, A. Olshen, E. Venkatraman, L. Norton, M. Wigler, Representational oligonucleotide microarray analysis: a high-resolution method to detect genome copy number variation. Genome Res 13, 2291-2305 (2003).
5. D. A. Peiffer, J. M. Le, F. J. Steemers, W. Chang, T. Jenniges, F. Garcia, K. Haden, J. Li, C. A. Shaw, J. Belmont, S. W. Cheung, R. M. Shen, D. L. Barker, K. L. Gunderson, High-resolution genomic profiling of chromosomal aberrations using Infinium whole-genome genotyping. Genome Res 16, 1136-1148 (2006).
6. T. L. Wang, C. Maierhofer, M. R. Speicher, C. Lengauer, B. Vogelstein, K. W. Kinzler, V. E. Velculescu, Digital karyotyping. Proc Natl Acad Sci USA 99, 16156-16161 (2002).
7. T. L. Wang, L. A. Diaz, Jr., K. Romans, A. Bardelli, S. Saha, G. Galizia, M. Choti, R. Donehower, G. Parmigiani, M. Shih Ie, C. Iacobuzio-Donahue, K. W. Kinzler, B. Vogelstein, C. Lengauer, V. E. Velculescu, Digital karyotyping identifies thymidylate synthase amplification as a mechanism of resistance to 5-fluorouracil in metastatic colorectal cancer patients. Proc Natl Acad Sci USA 101, 3089-3094 (2004).
8. C. Di, S. Liao, D. C. Adamson, T. J. Parrett, D. K. Broderick, Q. Shi, C. Lengauer, J. M. Cummins, V. E. Velculescu, D. W. Fults, R. E. McLendon, D. D. Bigner, H. Yan, Identification of OTX2 as a medulloblastoma oncogene whose product can be targeted by all-trans retinoic acid. Cancer Res 65, 919-924 (2005).
9. K. Nakayama, N. Nakayama, B. Davidson, H. Katabuchi, R. J. Kurman, V. E. Velculescu, M. Shih Ie, T. L. Wang, Homozygous deletion of MKK4 in ovarian serous carcinoma. Cancer Biol Ther 5, 630-634 (2006).
10. R. J. Leary, J. C. Lin, J. Cummins, S. Boca, L. D. Wood, D. W. Parsons, S. Jones, T. Sjoblom, B. H. Park, R. Parsons, J. Willis, D. Dawson, J. K. Willson, T. Nikolskaya, Y. Nikolsky, L. Kopelovich, N. Papadopoulos, L. A. Pennacchio, T. L. Wang, S. D. Markowitz, G. Parmigiani, K. W. Kinzler, B. Vogelstein, V. E. Velculescu, Integrated analysis of homozygous deletions, focal amplifications, and sequence alterations in breast and colorectal cancers. Proc Natl Acad Sci USA 105, 16224-16229 (2008).
11. D. Y. Chiang, G. Getz, D. B. Jaffe, M. J. O'Kelly, X. Zhao, S. L. Carter, C. Russ, C. Nusbaum, M. Meyerson, E. S. Lander, High-resolution mapping of copy-number alterations with massively parallel sequencing. Nat Methods 6, 99-103 (2009).
12. J. O. Korbel, A. E. Urban, J. P. Affourtit, B. Godwin, F. Grubert, J. F. Simons, P. M. Kim, D. Palejev, N. J. Carriero, L. Du, B. E. Taillon, Z. Chen, A. Tanzer, A. C. Saunders, J. Chi, F. Yang, N. P. Carter, M. E. Hurles, S. M. Weissman, T. T. Harkins, M. B. Gerstein, M. Egholm, M. Snyder, Paired-end mapping reveals extensive structural variation in the human genome. Science 318, 420-426 (2007).
13. P. J. Campbell, P. J. Stephens, E. D. Pleasance, S. O'Meara, H. Li, T. Santarius, L. A. Stebbings, C. Leroy, S. Edkins, C. Hardy, J. W. Teague, A. Menzies, I. Goodhead, D. J. Turner, C. M. Clee, M. A. Quail, A. Cox, C. Brown, R. Durbin, M. E. Hurles, P. A. Edwards, G. R. Bignell, M. R. Stratton, P. A. Futreal, Identification of somatically acquired rearrangements in cancer using genome-wide massively parallel paired-end sequencing. Nat Genet 40, 722-729 (2008).
14. C. A. Maher, C. Kumar-Sinha, X. Cao, S. Kalyana-Sundaram, B. Han, X. Jing, L. Sam, T. Barrette, N. Palanisamy, A. M. Chinnaiyan, Transcriptome sequencing to detect gene fusions in cancer. Nature 458, 97-101 (2009).
15. K. J. McKernan, H. E. Peckham, G. L. Costa, S. F. McLaughlin, Y. Fu, E. F. Tsung, C. R. Clouser, C. Duncan, J. K. Ichikawa, C. C. Lee, Z. Zhang, S. S. Ranade, E. T. Dimalanta, F. C. Hyland, T. D. Sokolsky, L. Zhang, A. Sheridan, H. Fu, C. L. Hendrickson, B. Li, L. Kotler, J. R. Stuart, J. A. Malek, J. M. Manning, A. A. Antipova, D. S. Perez, M. P. Moore, K. C. Hayashibara, M. R. Lyons, R. E. Beaudoin, B. E. Coleman, M. W. Laptewicz, A. E. Sannicandro, M. D. Rhodes, R. K. Gottimukkala, S. Yang, V. Bafna, A. Bashir, A. MacBride, C. Alkan, J. M. Kidd, E. E. Eichler, M. G. Reese, F. M. De La Vega, A. P. Blanchard, Sequence and structural variation in a human genome uncovered by short-read, massively parallel ligation sequencing using two-base encoding. Genome Res 19, 1527-1541 (2009).
16. D. Grimwade, J. V. Jovanovic, R. K. Hills, E. A. Nugent, Y. Patel, R. Flora, D. Diverio, K. Jones, H. Aslett, E. Batson, K. Rennie, R. Angell, R. E. Clark, E. Solomon, F. Lo-Coco, K. Wheatley, A. K. Burnett, Prospective minimal residual disease monitoring to predict relapse of acute promyelocytic leukemia and to direct pre-emptive arsenic trioxide therapy. J Clin Oncol 27, 3650-3658 (2009).
17. M. Bregni, S. Siena, A. Neri, R. Bassan, T. Barbui, D. Delia, G. Bonadonna, R. Dalla Favera, A. M. Gianni, Minimal residual disease in acute lymphoblastic leukemia detected by immune selection and gene rearrangement analysis. J Clin Oncol 7, 338-343 (1989).

18. V. H. van der Velden, E. R. Panzer-Grumayer, G. Cazzaniga, T. Flohr, R. Sutton, A. Schrauder, G. Basso, M. Schrappe, J. M. Wijkhuijs, M. Konrad, C. R. Bartram, G. Masera, A. Biondi, J. J. van Dongen, Optimization of PCR-based minimal residual disease diagnostics for childhood acute lymphoblastic leukemia in a multi-center setting. Leukemia 21, 706-713 (2007).
19. T. Lion, Minimal residual disease. Curr Opin Hematol 6, 406-411 (1999).
20. T. Hughes, M. Deininger, A. Hochhaus, S. Branford, J. Radich, J. Kaeda, M. Baccarani, J. Cortes, N. C. Cross, B. J. Druker, J. Gabert, D. Grimwade, R. Hehlmann, S. Kamel-Reid, J. H. Lipton, J. Longtine, G. Martinelli, G. Saglio, S. Soverini, W. Stock, J. M. Goldman, Monitoring CIVIL patients responding to treatment with tyrosine kinase inhibitors: review and recommendations for harmonizing current methodology for detecting BCR-ABL transcripts and kinase domain mutations and for expressing results. Blood 108, 28-37 (2006).
21. D. Dressman, H. Yan, G. Traverso, K. W. Kinzler, B. Vogelstein, Transforming single DNA molecules into fluorescent magnetic particles for detection and enumeration of genetic variations. Proc Natl Acad Sci USA 100, 8817-8822 (2003).
22. J. Shendure, G. J. Porreca, N. B. Reppas, X. Lin, J. P. McCutcheon, A. M. Rosenbaum, M. D. Wang, K. Zhang, R. D. Mitra, G. M. Church, Accurate multiplex polony sequencing of an evolved bacterial genome. Science 309, 1728-1732 (2005).
23. G. R. Bignell, T. Santarius, J. C. Pole, A. P. Butler, J. Perry, E. Pleasance, C. Greenman, A. Menzies, S. Taylor, S. Edkins, P. Campbell, M. Quail, B. Plumb, L. Matthews, K. McLay, P. A. Edwards, J. Rogers, R. Wooster, P. A. Futreal, M. R. Stratton. Genome Research 17:1296-1303 (2007).
24. P. J. Stephens, D. J. McBride, M. L. Lin, I. Varela, E. D. Pleasance, J. T. Simpson, L. A. Stebbings, C. Leroy, S. Edkins, L. J. Mudie, C. D. Greenman, M. Jia, C. Latimer, J. W. Teague, K. W. Lau, J. Burton, M. A. Quail, H. Swerdlow, C. Churcher, R. Natraj an, A. M. Sieuwerts, J. W. Martens, D. P. Silver, A. Langerod, H. E. Russnes, J. A. Foekens, J. S. Reis-Filho, L. van't Veer, A. L. Richardson, A. L. Borresen-Dale, P. J. Campbell, P. A. Futreal, M. R. Stratton. Complex landscapes of somatic rearrangement in human breast cancer genomes. Nature 462, 1005-1010 (2009).
25. M. Li, F. Diehl, D. Dressman, B. Vogelstein, K. W. Kinzler, BEAMing up for detection and quantification of rare sequence variants. Nat Methods 3, 95-97 (2006).
26. T. Sjoblom, S. Jones, L. D. Wood, D. W. Parsons, J. Lin, T. D. Barber, D. Mandelker, R. J. Leary, J. Ptak, N. Silliman, J. Szabo, P. Buckhaults, C. Farrell, P. Meeh, S. D. Markowitz, J. Willis, D. Dawson, J. K. Willson, A. F. Gazdar, J. Hartigan, L. Wu, C. Liu, G. Parmigiani, B. H. Park, K. E. Bachman, N. Papadopoulos, B. Vogelstein, K. W. Kinzler, V. E. Velculescu, The consensus coding sequences of human breast and colorectal cancers. Science 314, 268-274 (2006).
27. SOLiD Data format and File Definitions Guide. http://www3.appliedbiosystems.com/cms/groups/mcb_marketing/documents/generaldocuments/cms_058717.pdf
28. Primer 3 v. 0.4.0. http://frodo.wi.mit.edu/primer3/29. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz, Jr., Circulating mutant DNA to assess tumor dynamics. Nat Med 14, 985-990 (2008).

What is claimed is:

1. A method of monitoring a solid tumor in a human patient for minimal residual disease (MRD), comprising:
    (a) obtaining solid tumor DNA from a sample from a solid tumor from the human patient at a first time point;
    (b) contacting the solid tumor DNA obtained from the solid tumor sample from the human patient with amplification primers;
    (c) detecting one or more regions of copy number differences among regions of tumor DNA genome in the solid tumor DNA from the solid tumor sample;
    (d) preparing a mate-paired library of mate-paired DNA fragments from the solid tumor DNA obtained from the human patient, wherein the mate-paired DNA fragments comprise two genomic tags that are co-linear but not contiguous in a segment of tumor DNA;
    (e) assaying the mate-paired library by next-generation sequencing technologies to determine the sequences of the mate-paired DNA fragments;
    (f) identifying mate-paired tags that map within a region of copy number difference or that span a boundary of copy number difference, thereby identifying a tumor-specific somatic rearrangement comprising a rearrangement breakpoint or boundary in the solid tumor DNA from the solid tumor sample, wherein the tumor-specific somatic rearrangement is not present in DNA from non-tumor cells from the same human patient;
    (g) obtaining DNA from a biological sample from the human patients at a second time point, wherein the biological sample is selected from the group consisting of blood, stool, saliva, sputum, serum, and plasma;
    (h) monitoring the solid tumor in the human patient by performing polymerase chain reaction (PCR) using tumor rearrangement-specific amplification primers that amplify DNA fragments less than 200 base pairs (bp) in length, wherein the tumor rearrangement-specific amplification primers span or flank the rearrangement breakpoint or boundary identified in step (f) on the DNA obtained from the biological sample from the human patient, wherein an amplification product generated by the tumor rearrangement-specific amplification primers identifies the human patient as having MRD; and
    (i) treating the human patient identified as having MRD with surgery, chemotherapy, or radiation when MRD is present.

2. The method of claim 1, wherein the rearrangement breakpoint or boundary occurs between genes involved in rearrangements in less than 1% of solid tumors in human patients with the same type of solid tumor.

3. The method of claim 1, wherein identifying the tumor-specific somatic rearrangement further includes searching for mate-pair tags comprising mate-pairs that map to different chromosomes of a reference human genome.

4. The method of claim 1, wherein determining the region of copy number difference includes a digital karyotyping analysis.

5. The method of claim 4, wherein the digital karyotyping analysis includes mapping a plurality of genomic DNA tags to a reference genome and determining tag density ratios over a human reference genome within sliding windows of variable sizes to determine an amplified region that constitutes the region of copy number differences, wherein amplifications with tag density ratios 6 are identified as representing amplified regions that constitute a region of copy number differences.

6. The method of claim 1, wherein identifying the tumor-specific somatic rearrangement breakpoint comprises identifying mate-paired tags that map within the region of copy number differences.

7. The method of claim 1, wherein the tumor-specific somatic rearrangement is identified when two genomic tags of a mate-paired tag map to a reference human genome at positions selected from the group consisting of: (i) in different locations within a chromosome, (ii) in different orientations within a chromosome, and (iii) on different chromosomes.

8. The method of claim 1, wherein the tumor rearrangement-specific amplification primers hybridize to sites in the solid tumor DNA that flank the rearrangement breakpoint or boundary.

9. The method of claim 1, wherein the rearrangement breakpoint or boundary occurs between the same genes or the same gene loci in less than 0.1% of the human patients with the same type of solid tumor.

10. The method of claim 1, wherein a different copy number between two members of mate-paired tags indicates that the mate-paired tags span the breakpoint.

11. The method of claim 1, wherein performing the PCR on the biological sample from the human patient using the tumor rearrangement-specific amplification primers includes determining a quantity of the tumor DNA in the biological sample.

12. The method of claim 1, wherein multiple rearrangement breakpoints or boundaries are identified to provide a panel of rearrangement markers for the solid tumor, and PCR is performed using multiple pairs of tumor rearrangement-specific amplification primers that span the multiple rearrangement breakpoints or boundaries.

13. The method of claim 1, wherein the solid tumor sample from the human patient comprises a sample from a colorectal tumor or a breast tumor.

14. The method of claim 1, further comprising performing PCR multiple times after treatment to monitor the patient for MRD.

15. The method of claim 1, wherein the next generation sequencing technologies include sequencing by oligonucleotide ligation and detection (SOLiD).

* * * * *

UNITED STATES PATENT AND TRADEMARK OFFICE
CERTIFICATE OF CORRECTION

PATENT NO. : 10,900,088 B2
APPLICATION NO. : 15/950863
DATED : January 26, 2021
INVENTOR(S) : Bert Volgelstein et al.

Page 1 of 1

It is certified that error appears in the above-identified patent and that said Letters Patent is hereby corrected as shown below:

On the Title Page

Item [72] Lines 4-5, delete "Ellicot City, MD (US)" and insert -- Ellicott City, MD (US) --.

Item [56] Line 3, delete "continuation of application No. 13/579,964" and insert -- division of application No. 13/579,964 --.

Item [56] Line 14, delete "Analyeses," and insert -- Analysis, --.

In the Claims

Claim 5: Column 51, Line 7, delete "ratios 6" and insert -- ratios $\geq 6$ --.

Claim 15: Column 52, Line 23, delete "next generation" and insert -- next-generation --.

Signed and Sealed this
Eighth Day of June, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 92

<210> SEQ ID NO 1
<211> LENGTH: 25
<212> TYPE: DNA
<213> ORGANISM: Artificial Sequence
<220> FEATURE:
<223> OTHER INFORMATION: primers for human genome

<400> SEQUENCE: 1 aagttttttca agctttacct gaagt                                        25

<210> SEQ ID NO 2
<211> LENGTH: 20
<212> TYPE: DNA
<213> ORGANISM: Artificial Sequence
<220> FEATURE:
<223> OTHER INFORMATION: primers for human genome

<400> SEQUENCE: 2
agccaagtgc aattctccag                                               20

<210> SEQ ID NO 3
<211> LENGTH: 21
<212> TYPE: DNA
<213> ORGANISM: Artificial Sequence
<220> FEATURE:
<223> OTHER INFORMATION: primers for human genome

<400> SEQUENCE: 3
gccacctttc tttctttctg a           21

<210> SEQ ID NO 4
<211> LENGTH: 19
<212> TYPE: DNA
<213> ORGANISM: Artificial Sequence
<220> FEATURE:
<223> OTHER INFORMATION: primers for human genome

<400> SEQUENCE: 4
tggctttcaa aacccactg               19

<210> SEQ ID NO 5
<211> LENGTH: 20
<212> TYPE: DNA
<213> ORGANISM: Artificial Sequence
<220> FEATURE:
<223> OTHER INFORMATION: primers for human genome

<400> SEQUENCE: 5
tcatggttta tccacggtgt              20

<210> SEQ ID NO 6
<211> LENGTH: 21
<212> TYPE: DNA
<213> ORGANISM: Artificial Sequence
<220> FEATURE:
<223> OTHER INFORMATION: primers for human genome

<400> SEQUENCE: 6
tcaaaacaga aagcattagg c            21

<210> SEQ ID NO 7
<211> LENGTH: 21
<212> TYPE: DNA
<213> ORGANISM: Artificial Sequence
<220> FEATURE:
<223> OTHER INFORMATION: primers for human genome

<400> SEQUENCE: 7
aactcctccc acctcaaaat c            21

<210> SEQ ID NO 8
<211> LENGTH: 22
<212> TYPE: DNA
<213> ORGANISM: Artificial Sequence
<220> FEATURE:
<223> OTHER INFORMATION: primers for human genome

<400> SEQUENCE: 8
tgctaccaat acttcccact tg           22

<210> SEQ ID NO 9
<211> LENGTH: 23
<212> TYPE: DNA
<213> ORGANISM: Artificial Sequence
<220> FEATURE:
<223> OTHER INFORMATION: primers for human genome

<400> SEQUENCE: 9
ggagaaaacc ctggttattt tta          23

<210> SEQ ID NO 10
<211> LENGTH: 23
<212> TYPE: DNA
<213> ORGANISM: Artificial Sequence

```
<220> FEATURE:
<223> OTHER INFORMATION: primers for human genome

<400> SEQUENCE: 10
aaattgggaa ggatcatact gac                                          23

<210> SEQ ID NO 11
<211> LENGTH: 18
<212> TYPE: DNA
<213> ORGANISM: Artificial Sequence
<220> FEATURE:
<223> OTHER INFORMATION: primers for human genome

<400> SEQUENCE: 11
ctgaactcct gggctgaa                                                18

<210> SEQ ID NO 12
<211> LENGTH: 20
<212> TYPE: DNA
<213> ORGANISM: Artificial Sequence
<220> FEATURE:
<223> OTHER INFORMATION: primers for human genome

<400> SEQUENCE: 12
cctggcccct taggtaagat                                              20

<210> SEQ ID NO 13
<211> LENGTH: 21
<212> TYPE: DNA
<213> ORGANISM: Artificial Sequence
<220> FEATURE:
<223> OTHER INFORMATION: primers for human genome

<400> SEQUENCE: 13
tgcagctttt ctctgtcttc a                                            21

<210> SEQ ID NO 14
<211> LENGTH: 23
<212> TYPE: DNA
<213> ORGANISM: Artificial Sequence
<220> FEATURE:
<223> OTHER INFORMATION: primers for human genome

<400> SEQUENCE: 14
tgctgtttca aattcctaca gtc                                          23

<210> SEQ ID NO 15
<211> LENGTH: 21
<212> TYPE: DNA
<213> ORGANISM: Artificial Sequence
<220> FEATURE:
<223> OTHER INFORMATION: primers for human genome

<400> SEQUENCE: 15
gccaggtaac atgctcactt t                                            21

<210> SEQ ID NO 16
<211> LENGTH: 21
<212> TYPE: DNA
<213> ORGANISM: Artificial Sequence
<220> FEATURE:
<223> OTHER INFORMATION: primers for human genome

<400> SEQUENCE: 16
gggctaagct taagagtctg g                                            21
```

<210> SEQ ID NO 17
<211> LENGTH: 18
<212> TYPE: DNA
<213> ORGANISM: Artificial Sequence
<220> FEATURE:
<223> OTHER INFORMATION: primers for human genome

<400> SEQUENCE: 17
tctgccggca tactggac                                                 18

<210> SEQ ID NO 18
<211> LENGTH: 24
<212> TYPE: DNA
<213> ORGANISM: Artificial Sequence
<220> FEATURE:
<223> OTHER INFORMATION: primers for human genome

<400> SEQUENCE: 18
gccctatttt cagagaaagt ggta                                          24

<210> SEQ ID NO 19
<211> LENGTH: 23
<212> TYPE: DNA
<213> ORGANISM: Artificial Sequence
<220> FEATURE:
<223> OTHER INFORMATION: primers for human genome

<400> SEQUENCE: 19
aatttgctct catcgtattg tgt                                           23

<210> SEQ ID NO 20
<211> LENGTH: 22
<212> TYPE: DNA
<213> ORGANISM: Artificial Sequence
<220> FEATURE:
<223> OTHER INFORMATION: primers for human genome

<400> SEQUENCE: 20
ctgaatctct ttccagcaaa at                                            22

<210> SEQ ID NO 21
<211> LENGTH: 20
<212> TYPE: DNA
<213> ORGANISM: Artificial Sequence
<220> FEATURE:
<223> OTHER INFORMATION: primers for human genome

<400> SEQUENCE: 21
tagcatgcac cactttaggc                                               20

<210> SEQ ID NO 22
<211> LENGTH: 19
<212> TYPE: DNA
<213> ORGANISM: Artificial Sequence
<220> FEATURE:
<223> OTHER INFORMATION: primers for human genome

<400> SEQUENCE: 22
ggttctggag ggttggaga                                                19

<210> SEQ ID NO 23
<211> LENGTH: 20
<212> TYPE: DNA
<213> ORGANISM: Artificial Sequence
<220> FEATURE:
<223> OTHER INFORMATION: primers for human genome

```
<400> SEQUENCE: 23
tatgccacca tcgcttaggt                                               20

<210> SEQ ID NO 24
<211> LENGTH: 21
<212> TYPE: DNA
<213> ORGANISM: Artificial Sequence
<220> FEATURE:
<223> OTHER INFORMATION: primers for human genome

<400> SEQUENCE: 24
ggtgttctct ctcccatacc a                                             21

<210> SEQ ID NO 25
<211> LENGTH: 21
<212> TYPE: DNA
<213> ORGANISM: Artificial Sequence
<220> FEATURE:
<223> OTHER INFORMATION: primers for human genome

<400> SEQUENCE: 25
tgcttttagt tttgggtacg g                                             21

<210> SEQ ID NO 26
<211> LENGTH: 20
<212> TYPE: DNA
<213> ORGANISM: Artificial Sequence
<220> FEATURE:
<223> OTHER INFORMATION: primers for human genome

<400> SEQUENCE: 26
atcctcggac tggactgaga                                               20

<210> SEQ ID NO 27
<211> LENGTH: 21
<212> TYPE: DNA
<213> ORGANISM: Artificial Sequence
<220> FEATURE:
<223> OTHER INFORMATION: primers for human genome

<400> SEQUENCE: 27
gggttatctc aaaagggcag a                                             21

<210> SEQ ID NO 28
<211> LENGTH: 23
<212> TYPE: DNA
<213> ORGANISM: Artificial Sequence
<220> FEATURE:
<223> OTHER INFORMATION: primers for human genome

<400> SEQUENCE: 28
tgtgttcctc tcctcttaag cat                                           23

<210> SEQ ID NO 29
<211> LENGTH: 18
<212> TYPE: DNA
<213> ORGANISM: Artificial Sequence
<220> FEATURE:
<223> OTHER INFORMATION: primers for human genome

<400> SEQUENCE: 29
atccccacat tcccaacc                                                 18

<210> SEQ ID NO 30
```

```
<211> LENGTH: 26
<212> TYPE: DNA
<213> ORGANISM: Artificial Sequence
<220> FEATURE:
<223> OTHER INFORMATION: primers for human genome

<400> SEQUENCE: 30
gtatttgttc atgtttgtta ggtgtt                                          26

<210> SEQ ID NO 31
<211> LENGTH: 20
<212> TYPE: DNA
<213> ORGANISM: Artificial Sequence
<220> FEATURE:
<223> OTHER INFORMATION: primers for human genome

<400> SEQUENCE: 31
acgtgtgtat tgggggtagc                                                 20

<210> SEQ ID NO 32
<211> LENGTH: 21
<212> TYPE: DNA
<213> ORGANISM: Artificial Sequence
<220> FEATURE:
<223> OTHER INFORMATION: primers for human genome

<400> SEQUENCE: 32
agctaggtgg agaatttgtc g                                               21

<210> SEQ ID NO 33
<211> LENGTH: 23
<212> TYPE: DNA
<213> ORGANISM: Artificial Sequence
<220> FEATURE:
<223> OTHER INFORMATION: primers for human genome

<400> SEQUENCE: 33
aaggagattg gttattgtgg aaa                                             23

<210> SEQ ID NO 34
<211> LENGTH: 21
<212> TYPE: DNA
<213> ORGANISM: Artificial Sequence
<220> FEATURE:
<223> OTHER INFORMATION: primers for human genome

<400> SEQUENCE: 34
tgctgaatca ttctcccaac t                                               21

<210> SEQ ID NO 35
<211> LENGTH: 24
<212> TYPE: DNA
<213> ORGANISM: Artificial Sequence
<220> FEATURE:
<223> OTHER INFORMATION: primers for human genome

<400> SEQUENCE: 35
gcattctaaa gatgaagtcc catt                                            24

<210> SEQ ID NO 36
<211> LENGTH: 26
<212> TYPE: DNA
<213> ORGANISM: Artificial Sequence
<220> FEATURE:
<223> OTHER INFORMATION: primers for human genome

<400> SEQUENCE: 36
```

```
caggtgatat accaaagaaa attagg                                              26
```

```
<210> SEQ ID NO 37
<211> LENGTH: 19
<212> TYPE: DNA
<213> ORGANISM: Artificial Sequence
<220> FEATURE:
<223> OTHER INFORMATION: primers for human genome

<400> SEQUENCE: 37
agtcaacgcc ctagcatgg                                                      19
```

```
<210> SEQ ID NO 38
<211> LENGTH: 20
<212> TYPE: DNA
<213> ORGANISM: Artificial Sequence
<220> FEATURE:
<223> OTHER INFORMATION: primers for human genome

<400> SEQUENCE: 38
aatcacgttg ggtgactgtg                                                     20
```

```
<210> SEQ ID NO 39
<211> LENGTH: 20
<212> TYPE: DNA
<213> ORGANISM: Artificial Sequence
<220> FEATURE:
<223> OTHER INFORMATION: primers for human genome

<400> SEQUENCE: 39
tgaaggttga gttgccagtg                                                     20
```

```
<210> SEQ ID NO 40
<211> LENGTH: 22
<212> TYPE: DNA
<213> ORGANISM: Artificial Sequence
<220> FEATURE:
<223> OTHER INFORMATION: primers for human genome

<400> SEQUENCE: 40
aggaggaaag caacacatag ag                                                  22
```

```
<210> SEQ ID NO 41
<211> LENGTH: 21
<212> TYPE: DNA
<213> ORGANISM: Artificial Sequence
<220> FEATURE:
<223> OTHER INFORMATION: primers for human genome

<400> SEQUENCE: 41
aattaccaca actcccagca g                                                   21
```

```
<210> SEQ ID NO 42
<211> LENGTH: 21
<212> TYPE: DNA
<213> ORGANISM: Artificial Sequence
<220> FEATURE:
<223> OTHER INFORMATION: primers for human genome

<400> SEQUENCE: 42
tgaatcagaa agtctggcag t                                                   21
```

```
<210> SEQ ID NO 43
<211> LENGTH: 20
<212> TYPE: DNA
```

<213> ORGANISM: Artificial Sequence
<220> FEATURE:
<223> OTHER INFORMATION: primers for human genome

<400> SEQUENCE: 43
cctagccctt tgttccctgt                                               20

<210> SEQ ID NO 44
<211> LENGTH: 22
<212> TYPE: DNA
<213> ORGANISM: Artificial Sequence
<220> FEATURE:
<223> OTHER INFORMATION: primers for human genome

<400> SEQUENCE: 44
gcagagaaca gcagaaaagt tg                                            22

<210> SEQ ID NO 45
<211> LENGTH: 22
<212> TYPE: DNA
<213> ORGANISM: Artificial Sequence
<220> FEATURE:
<223> OTHER INFORMATION: primers for human genome

<400> SEQUENCE: 45
ttctctttct ctgccttcag tg                                            22

<210> SEQ ID NO 46
<211> LENGTH: 18
<212> TYPE: DNA
<213> ORGANISM: Artificial Sequence
<220> FEATURE:
<223> OTHER INFORMATION: primers for human genome

<400> SEQUENCE: 46
ggctcccctc tccattcc                                                 18

<210> SEQ ID NO 47
<211> LENGTH: 26
<212> TYPE: DNA
<213> ORGANISM: Artificial Sequence
<220> FEATURE:
<223> OTHER INFORMATION: primers for human genome

<400> SEQUENCE: 47
tatattggaa gaatagaaat gaatgg                                        26

<210> SEQ ID NO 48
<211> LENGTH: 20
<212> TYPE: DNA
<213> ORGANISM: Artificial Sequence
<220> FEATURE:
<223> OTHER INFORMATION: primers for human genome

<400> SEQUENCE: 48
gcacactgtt tgcaggaatg                                               20

<210> SEQ ID NO 49
<211> LENGTH: 22
<212> TYPE: DNA
<213> ORGANISM: Artificial Sequence
<220> FEATURE:
<223> OTHER INFORMATION: primers for human genome

<400> SEQUENCE: 49
aagctttgtt tggttgttct ca                                            22

<210> SEQ ID NO 50
<211> LENGTH: 19
<212> TYPE: DNA
<213> ORGANISM: Artificial Sequence
<220> FEATURE:
<223> OTHER INFORMATION: primers for human genome

<400> SEQUENCE: 50
tcctttctgc ccattaggg                                              19

<210> SEQ ID NO 51
<211> LENGTH: 20
<212> TYPE: DNA
<213> ORGANISM: Artificial Sequence
<220> FEATURE:
<223> OTHER INFORMATION: primers for human genome

<400> SEQUENCE: 51
cacaccgcat tcacacaaac                                             20

<210> SEQ ID NO 52
<211> LENGTH: 23
<212> TYPE: DNA
<213> ORGANISM: Artificial Sequence
<220> FEATURE:
<223> OTHER INFORMATION: primers for human genome

<400> SEQUENCE: 52
cgcatccaaa gtattaatag caa                                         23

<210> SEQ ID NO 53
<211> LENGTH: 22
<212> TYPE: DNA
<213> ORGANISM: Artificial Sequence
<220> FEATURE:
<223> OTHER INFORMATION: primers for human genome

<400> SEQUENCE: 53
ccaaattgcc tgcttaagag at                                          22

<210> SEQ ID NO 54
<211> LENGTH: 19
<212> TYPE: DNA
<213> ORGANISM: Artificial Sequence
<220> FEATURE:
<223> OTHER INFORMATION: primers for human genome

<400> SEQUENCE: 54
taccgtcctc caggcatgt                                              19

<210> SEQ ID NO 55
<211> LENGTH: 20
<212> TYPE: DNA
<213> ORGANISM: Artificial Sequence
<220> FEATURE:
<223> OTHER INFORMATION: primers for human genome

<400> SEQUENCE: 55
tccctcatca gagcaaatca                                             20

<210> SEQ ID NO 56
<211> LENGTH: 22
<212> TYPE: DNA
<213> ORGANISM: Artificial Sequence
<220> FEATURE:

<223> OTHER INFORMATION: primers for human genome

<400> SEQUENCE: 56
tctgaacatg cctgatctca tc                    22

<210> SEQ ID NO 57
<211> LENGTH: 22
<212> TYPE: DNA
<213> ORGANISM: Artificial Sequence
<220> FEATURE:
<223> OTHER INFORMATION: primers for human genome

<400> SEQUENCE: 57
ttgctaagtg atgctacctg tg                    22

<210> SEQ ID NO 58
<211> LENGTH: 24
<212> TYPE: DNA
<213> ORGANISM: Artificial Sequence
<220> FEATURE:
<223> OTHER INFORMATION: primers for human genome

<400> SEQUENCE: 58
tgaagaatcc ttctagtgat ggaa                  24

<210> SEQ ID NO 59
<211> LENGTH: 19
<212> TYPE: DNA
<213> ORGANISM: Artificial Sequence
<220> FEATURE:
<223> OTHER INFORMATION: primers for human genome

<400> SEQUENCE: 59
ctgccagtcc aaactggtg                        19

<210> SEQ ID NO 60
<211> LENGTH: 21
<212> TYPE: DNA
<213> ORGANISM: Artificial Sequence
<220> FEATURE:
<223> OTHER INFORMATION: primers for human genome

<400> SEQUENCE: 60
tgaaattagg acctggagca c                     21

<210> SEQ ID NO 61
<211> LENGTH: 20
<212> TYPE: DNA
<213> ORGANISM: Artificial Sequence
<220> FEATURE:
<223> OTHER INFORMATION: primers for human genome

<400> SEQUENCE: 61
gatgcaggaa gttgacagca                       20

<210> SEQ ID NO 62
<211> LENGTH: 20
<212> TYPE: DNA
<213> ORGANISM: Artificial Sequence
<220> FEATURE:
<223> OTHER INFORMATION: primers for human genome

<400> SEQUENCE: 62
gccatgtgca agtcaagaag                       20

```
<210> SEQ ID NO 63
<211> LENGTH: 20
<212> TYPE: DNA
<213> ORGANISM: Artificial Sequence
<220> FEATURE:
<223> OTHER INFORMATION: primers for human genome

<400> SEQUENCE: 63
taagggcgat gtgaacaagg                                               20

<210> SEQ ID NO 64
<211> LENGTH: 24
<212> TYPE: DNA
<213> ORGANISM: Artificial Sequence
<220> FEATURE:
<223> OTHER INFORMATION: primers for human genome

<400> SEQUENCE: 64
aacatctctt cctttttgaag atcc                                         24

<210> SEQ ID NO 65
<211> LENGTH: 22
<212> TYPE: DNA
<213> ORGANISM: Artificial Sequence
<220> FEATURE:
<223> OTHER INFORMATION: primers for human genome

<400> SEQUENCE: 65
agctgaatca aaatttccaa tg                                            22

<210> SEQ ID NO 66
<211> LENGTH: 21
<212> TYPE: DNA
<213> ORGANISM: Artificial Sequence
<220> FEATURE:
<223> OTHER INFORMATION: primers for human genome

<400> SEQUENCE: 66
aatgggttaa gcagtttagg g                                             21

<210> SEQ ID NO 67
<211> LENGTH: 26
<212> TYPE: DNA
<213> ORGANISM: Artificial Sequence
<220> FEATURE:
<223> OTHER INFORMATION: primers for human genome

<400> SEQUENCE: 67
aaaggttaaa ggactgtttt aagttg                                        26

<210> SEQ ID NO 68
<211> LENGTH: 26
<212> TYPE: DNA
<213> ORGANISM: Artificial Sequence
<220> FEATURE:
<223> OTHER INFORMATION: primers for human genome

<400> SEQUENCE: 68
gttaagatca acattttgt ttcaag                                         26

<210> SEQ ID NO 69
<211> LENGTH: 20
<212> TYPE: DNA
<213> ORGANISM: Artificial Sequence
<220> FEATURE:
<223> OTHER INFORMATION: primers for human genome
```

```
<400> SEQUENCE: 69
tcccagtgca ataaaaccaa                                               20

<210> SEQ ID NO 70
<211> LENGTH: 21
<212> TYPE: DNA
<213> ORGANISM: Artificial Sequence
<220> FEATURE:
<223> OTHER INFORMATION: primers for human genome

<400> SEQUENCE: 70
cgatctatac accaccccac a                                             21

<210> SEQ ID NO 71
<211> LENGTH: 23
<212> TYPE: DNA
<213> ORGANISM: Artificial Sequence
<220> FEATURE:
<223> OTHER INFORMATION: primers for human genome

<400> SEQUENCE: 71
gctgatttgt ttatacccag tgc                                           23

<210> SEQ ID NO 72
<211> LENGTH: 20
<212> TYPE: DNA
<213> ORGANISM: Artificial Sequence
<220> FEATURE:
<223> OTHER INFORMATION: primers for human genome

<400> SEQUENCE: 72
aaccccatcc tgaagctacc                                               20

<210> SEQ ID NO 73
<211> LENGTH: 22
<212> TYPE: DNA
<213> ORGANISM: Artificial Sequence
<220> FEATURE:
<223> OTHER INFORMATION: primers for human genome

<400> SEQUENCE: 73
gctctcaatt tgtgtgattt gg                                            22

<210> SEQ ID NO 74
<211> LENGTH: 21
<212> TYPE: DNA
<213> ORGANISM: Artificial Sequence
<220> FEATURE:
<223> OTHER INFORMATION: primers for human genome

<400> SEQUENCE: 74
gactacaaat ggcccagact c                                             21

<210> SEQ ID NO 75
<211> LENGTH: 20
<212> TYPE: DNA
<213> ORGANISM: Artificial Sequence
<220> FEATURE:
<223> OTHER INFORMATION: primers for human genome

<400> SEQUENCE: 75
cccagccata tgttggttta                                               20

<210> SEQ ID NO 76
<211> LENGTH: 19
```

```
<212> TYPE: DNA
<213> ORGANISM: Artificial Sequence
<220> FEATURE:
<223> OTHER INFORMATION: primers for human genome

<400> SEQUENCE: 76
tcaatggggg agagagagc                                                   19

<210> SEQ ID NO 77
<211> LENGTH: 22
<212> TYPE: DNA
<213> ORGANISM: Artificial Sequence
<220> FEATURE:
<223> OTHER INFORMATION: primers for human genome

<400> SEQUENCE: 77
ccagatggct gggttaaata aa                                               22

<210> SEQ ID NO 78
<211> LENGTH: 22
<212> TYPE: DNA
<213> ORGANISM: Artificial Sequence
<220> FEATURE:
<223> OTHER INFORMATION: primers for human genome

<400> SEQUENCE: 78
ggcttctgta gagtgcacat ga                                               22

<210> SEQ ID NO 79
<211> LENGTH: 22
<212> TYPE: DNA
<213> ORGANISM: Artificial Sequence
<220> FEATURE:
<223> OTHER INFORMATION: primers for human genome

<400> SEQUENCE: 79
ctgcaggaac tgtctcattc tt                                               22

<210> SEQ ID NO 80
<211> LENGTH: 20
<212> TYPE: DNA
<213> ORGANISM: Artificial Sequence
<220> FEATURE:
<223> OTHER INFORMATION: primers for human genome

<400> SEQUENCE: 80
tggtgattcc actgaggtga                                                  20

<210> SEQ ID NO 81
<211> LENGTH: 22
<212> TYPE: DNA
<213> ORGANISM: Artificial Sequence
<220> FEATURE:
<223> OTHER INFORMATION: primers for human genome

<400> SEQUENCE: 81
ggaaaccgtt agtggaaaag tc                                               22

<210> SEQ ID NO 82
<211> LENGTH: 24
<212> TYPE: DNA
<213> ORGANISM: Artificial Sequence
<220> FEATURE:
<223> OTHER INFORMATION: primers for human genome

<400> SEQUENCE: 82
```
tttgggttca gttctatttg aaga                                              24

<210> SEQ ID NO 83
<211> LENGTH: 20
<212> TYPE: DNA
<213> ORGANISM: Artificial Sequence
<220> FEATURE:
<223> OTHER INFORMATION: primers for human genome

<400> SEQUENCE: 83
tgggcatgag caagatattc                                                    20

<210> SEQ ID NO 84
<211> LENGTH: 18
<212> TYPE: DNA
<213> ORGANISM: Artificial Sequence
<220> FEATURE:
<223> OTHER INFORMATION: primers for human genome

<400> SEQUENCE: 84
gtgacaggct gggtgtcc                                                      18

<210> SEQ ID NO 85
<211> LENGTH: 24
<212> TYPE: DNA
<213> ORGANISM: Artificial Sequence
<220> FEATURE:
<223> OTHER INFORMATION: primers for human genome

<400> SEQUENCE: 85
tgtatgaaac attgtagagg ctgt                                               24

<210> SEQ ID NO 86
<211> LENGTH: 23
<212> TYPE: DNA
<213> ORGANISM: Artificial Sequence
<220> FEATURE:
<223> OTHER INFORMATION: primers for human genome

<400> SEQUENCE: 86
ggtgattttc aatgcatatt tca                                                23

<210> SEQ ID NO 87
<211> LENGTH: 22
<212> TYPE: DNA
<213> ORGANISM: Artificial Sequence
<220> FEATURE:
<223> OTHER INFORMATION: primers for human genome

<400> SEQUENCE: 87
caaaagattt ccaaatgcag gt                                                 22

<210> SEQ ID NO 88
<211> LENGTH: 24
<212> TYPE: DNA
<213> ORGANISM: Artificial Sequence
<220> FEATURE:
<223> OTHER INFORMATION: primers for human genome

<400> SEQUENCE: 88
cacttgagaa tcaatgatat gcag                                               24

<210> SEQ ID NO 89
<211> LENGTH: 25
<212> TYPE: DNA
<213> ORGANISM: Artificial Sequence

```
<220> FEATURE:
<223> OTHER INFORMATION: primers for human genome

<400> SEQUENCE: 89
tttgtgtacc tagacattca tccaa                                              25

<210> SEQ ID NO 90
<211> LENGTH: 20
<212> TYPE: DNA
<213> ORGANISM: Artificial Sequence
<220> FEATURE:
<223> OTHER INFORMATION: primers for human genome

<400> SEQUENCE: 90
agccaagatc aagccacaga                                                    20

<210> SEQ ID NO 91
<211> LENGTH: 26
<212> TYPE: DNA
<213> ORGANISM: Artificial Sequence
<220> FEATURE:
<223> OTHER INFORMATION: primers for human genome

<400> SEQUENCE: 91
ttgatgattt agaaactcta gcctgt                                             26

<210> SEQ ID NO 92
<211> LENGTH: 19
<212> TYPE: DNA
<213> ORGANISM: Artificial Sequence
<220> FEATURE:
<223> OTHER INFORMATION: primers for human genome

<400> SEQUENCE: 92
ctgctgacgt gctggtctt                                                     19
```